(12) United States Patent
Galindo Casas et al.

(10) Patent No.: US 12,104,188 B2
(45) Date of Patent: Oct. 1, 2024

(54) MODIFIED CASPASE-9 POLYPEPTIDES AND METHODS OF USE THEREOF

(71) Applicant: Allogene Therapeutics, Inc., South San Francisco, CA (US)

(72) Inventors: Meritxell Galindo Casas, Graz (AT); Thomas John Van Blarcom, Oakland, CA (US)

(73) Assignee: Allogene Therapeutics, Inc., South San Francisco, CA (US)

( * ) Notice: Subject to any disclaimer, the term of this patent is extended or adjusted under 35 U.S.C. 154(b) by 1 day.

(21) Appl. No.: 17/716,253

(22) Filed: Apr. 8, 2022

(65) Prior Publication Data

US 2022/0235346 A1 Jul. 28, 2022

Related U.S. Application Data

(62) Division of application No. 16/177,280, filed on Oct. 31, 2018, now Pat. No. 11,326,156.

(60) Provisional application No. 62/592,447, filed on Nov. 30, 2017, provisional application No. 62/580,276, filed on Nov. 1, 2017.

(51) Int. Cl.
| | |
|---|---|
| *C12N 9/64* | (2006.01) |
| *A61K 31/7088* | (2006.01) |
| *A61K 35/17* | (2015.01) |
| *A61K 38/48* | (2006.01) |
| *A61K 38/52* | (2006.01) |
| *C12N 5/0783* | (2010.01) |
| *C12N 9/90* | (2006.01) |
| *C12N 11/18* | (2006.01) |

(52) U.S. Cl.
CPC ........ *C12N 9/6472* (2013.01); *A61K 31/7088* (2013.01); *A61K 35/17* (2013.01); *A61K 38/4873* (2013.01); *A61K 38/52* (2013.01); *C12N 5/0636* (2013.01); *C12N 9/90* (2013.01); *C12N 11/18* (2013.01); *C12Y 304/22062* (2013.01); *C12Y 502/01008* (2013.01); *C07K 2319/50* (2013.01); *C07K 2319/70* (2013.01); *C12N 2501/734* (2013.01); *C12N 2510/00* (2013.01); *C12N 2740/16043* (2013.01)

(58) Field of Classification Search
CPC ...... C12N 9/6472; C12N 5/0636; C12N 9/90; C12N 11/18; C12N 2501/734; C12N 2510/00; C12N 2740/16043; A61K 31/7088; A61K 35/17; A61K 38/4873; C12Y 304/22062; C12Y 502/01008
See application file for complete search history.

(56) References Cited

U.S. PATENT DOCUMENTS 9,434,935 B2   9/2016   Spencer et al.

FOREIGN PATENT DOCUMENTS

| WO | WO2014197638 A2 | 12/2014 |
| WO | WO2016071758 A1 | 5/2015 |
| WO | WO2015134877 A1 | 9/2015 |

OTHER PUBLICATIONS

Bratton, Shawn B., et al., "Recruitment, activation and retention of caspases-9 and -3 by Apaf-1 apoptosome and associated XIAP complexes", EMBO J. Mar. 1, 2001; 20(5): 998-1009; doi: 10.1093/emboj/20.5.998.
Chao, Yang , et al., "Engineering a Dimeric Caspase-9: Model for Caspase Activation", PLoS Biol. Jun. 2005;3(6): e183. doi: 10.1371/journal.pbio.0030183. Epub May 10, 2005.
EPO , "International Search Report and Written Opinion", Mailed on Mar. 14, 2019 for PCT/US2018/058573; 25 pages.
EPO , "Office Action Mailed on Sep. 27, 2021 for EP 18808161.6; 31 pages".
Gargett, Tessa , et al., "The inducible caspase-9 suicide gene system as a "safety switch" to limit on-target, off-tumor toxicities of chimeric antigen receptor T cells", Front Pharmacol. 2014;5:235. Published Oct. 28, 2014. doi:10.3389/fphar.2014.00235.
Li, Ping , et al., "Caspase-9: structure, mechanisms and clinical application", Oncotarget. 2017; 8:23996-24008. https://doi.org/10.18632/oncotarget.15098.
Li, Yini , et al., "Mechanistic insights into caspase-9 activation by the structure of the apoptosome holoenzyme", PNAS Feb. 14, 2017 114 (7) 1542-1547; first published Jan. 31, 2017; https://doi.org/10.1073/pnas.1620626114.
Shiozaki, Eric N., et al., "Mechanism of XIAP-Mediated Inhibition of Caspase-9", Molecular Cell, vol. 11, 519-527, Feb. 2003.
Silke, John , et al., "Inhibitor of Apoptosis (IAP) Proteins—Modulators of Cell Death and Inflammation", Cold Spring Harb Perspect Biol. Feb. 1, 2013;5(2):a008730. doi: 10.1101/cshperspect.a008730.
Yin, Qian , "Caspase-9 holoenzyme is a specific and optimal pro-caspase-3 processing machine", Mol Cell. Apr. 21, 2006; 22(2): 259-268. doi:10.1016/j.molcel.2006.03.030.
Zamaraev, Alexey V., "Post-translational Modification of Caspases: The Other Side of Apoptosis Regulation", Trends in Cell Biology, May 2017, vol. 27, No. 5 http://dx.doi.org/10.1016/j.tcb.2017.01.003.

*Primary Examiner* — Iqbal H Chowdhury
(74) *Attorney, Agent, or Firm* — Allogene Therapeutics, Inc.

(57) ABSTRACT

Provided herein are modified caspase-9 polypeptides, and chimeric caspase-9 proteins containing the modified caspase-9 polypeptides. The disclosure further provides polynucleotides encoding these proteins, engineered host cells containing these polynucleotides and proteins, including host cells that co-express a chimeric antigen receptor, and methods of making and using the same.

35 Claims, 8 Drawing Sheets
Specification includes a Sequence Listing.

MODIFIED CASPASE-9 POLYPEPTIDES AND METHODS OF USE THEREOF

CROSS-REFERENCE TO RELATED APPLICATIONS

This application is a divisional of U.S. application Ser. No. 16/177,280 filed on Oct. 31, 2018, now U.S. Pat. No. 11,326,156, which claims the benefit of priority to U.S. Provisional Application Ser. No. 62/580,276, filed Nov. 1, 2017, and U.S. Provisional Application Ser. No. 62/592,447, filed Nov. 30, 2017, each of which is incorporated by reference herein in its entirety for all purposes.

REFERENCE TO SEQUENCE LISTING

This application is being filed electronically via EFS-Web and includes an electronically submitted sequence listing in .txt format. The .txt file contains a sequence listing entitled "AT-013_04US_SL.txt" created on Dec. 21, 2021 and having a size of 24,810 bytes. The sequence listing contained in this .txt file is part of the specification and is incorporated herein by reference in its entirety.

FIELD

This disclosure relates to modified caspase-9 polypeptides and uses thereof. The modified caspase-9 polypeptides provided herein contain at least 1 amino acid mutation as compared to the wild-type human caspase-9 protein.

BACKGROUND

Caspase 9 is a protein that is involved in the initiation of apoptosis (programmed cell death) in mammalian cells. Chimeric proteins that contain a caspase-9 portion can be used as part of a system which permits induced apoptosis in host cells engineered to express this chimeric protein. For example, a chimeric protein can be prepared which contains a caspase-9 polypeptide linked with a ligand-mediated dimerization domain. Exposure of host cells containing this chimeric protein with a ligand which mediates dimerization of the dimerization domain results in activation of caspase-9 signaling in the host cell, leading to apoptosis and cell death. This system may be used, for example, as a safety mechanism for cellular therapies. In this system, a host cell to be administered to a subject is first engineered to express the caspase-9 containing chimeric protein. Then, after the engineered host cell is introduced into the subject, the subject may be administered the dimerization-inducing ligand, if needed (e.g. in the event the host cell is causing a serious, undesirable effects in the subject). Administration of the ligand to the subject results in activation of caspase-9 signaling in host cells containing the chimeric protein and subsequent death of such host cells, thereby reducing the undesirable effects of the host cells in the subject (see, e.g. Gargett T and Brown M, Front Pharmacol. 2014; 5: 235).

In some circumstances, a chimeric protein that contains a caspase-9 polypeptide and a dimerization domain may have an undesirably high level of basal caspase-9 activity in host cells that express the chimeric protein (i.e. the chimeric protein may have activity in the absence of the ligand which mediates dimerization). The basal caspase-9 activity may result in, for example, an undesirable level of cell death in the absence of the ligand.

One possible approach to reduce the basal caspase-9 activity in chimeric caspase-9 proteins is to introduce one or more modifications in the caspase-9 portion of a chimeric caspase-9 protein. For example, one or more mutations may be introduced in the amino acid sequence of the caspase-9 polypeptide in a chimeric caspase-9 protein. Ideally, such modifications will reduce the basal caspase-9 activity in the chimeric protein, but will not reduce or will only slightly reduce the caspase-9 activity of the chimeric protein in response to the dimerization-inducing ligand. Examples of some mutations which reduce the basal activity of caspase-9 polypeptides are described, for example, in U.S. Pat. No. 9,434,935.

However, there remains a need for alternative and improved modified caspase-9 polypeptides. Alternative and improved modified caspase-9 polypeptides may provide, for example, alternative and improved compositions and methods for cellular therapies.

SUMMARY

Provided herein are modified caspase-9 polypeptides and uses thereof. The modified caspase-9 polypeptides may have one or more useful property as compared to a corresponding non-modified caspase-9 polypeptide.

For example, in some embodiments provide herein, modified capase-9 polypeptides are provided in which the modified caspase-9 polypeptide has reduced basal activity as compared to a corresponding non-modified capase-9 polypeptide, but in which the modified caspase-9 polypeptide can also still effectively mediate caspase-9 signaling.

In some embodiments provided herein, modified caspase-9 polypeptides are provided, wherein when the modified capase-9 polypeptide is incorporated into a chimeric caspase-9 protein containing a capase-9 polypeptide and a ligand-inducible dimerization domain. A chimeric caspase-9 protein containing a modified caspase-9 polypeptide provided herein may have reduced basal activity as compared to a corresponding chimeric caspase-9 protein that contains a wild-type caspase-9 polypeptide.

In some embodiments, provided herein is a modified caspase-9 polypeptide comprising an amino acid sequence having at least 90% sequence identity to SEQ ID NO: 2, and at least one amino acid substitution, wherein the amino acid substitution is at an amino acid position selected from the group consisting of S271, S274, D330, F342, I370, D379, V387, A390, F406, and K409. Optionally, the amino acid substitution is selected from the group consisting of S271Y, S274E, D330L, D330M, F342H, I370E, D379E, V387A, A390N, F406W, and K409N. Optionally, the polypeptide comprises at least two amino acid substitutions, wherein the amino acid substitutions are at the amino acid positions selected from the group consisting of Q221-V387, D330-I370, D330-D379, D330-S271, D330-S274, D330-F342, D330-D379, D330-V387, D330-A390, and D330-K409. Optionally, the polypeptide comprises at least two amino acid substitutions selected from the group consisting of Q221R-V387A, D330L-I370E, D330L-D379E, D330M-S271Y, D330M-S274E, D330M-F342H, D330M-I370E, D330M-D379E, D330M-V387A, D330M-A390N, and D330M-K409N.

In some embodiments, provided herein is a modified caspase-9 polypeptide comprising an amino acid sequence having at least 90% sequence identity to SEQ ID NO: 2, and at least the amino acid substitutions D330M-D379E (i.e. D330M and D379E).

In some embodiments, provided herein is a modified caspase-9 polypeptide comprising an amino acid sequence having at least 70%, 80%, 90% 95%, 97%, 98%, or 99% sequence identity to SEQ ID NO: 2, and at least one amino acid substitution selected from the group consisting of S271Y, S274E, D330L, D330M, F342H, I370E, D379E, V387A, A390N, F406W, and K409N. Optionally, the modified caspase-9 polypeptide comprises at least two amino acid substitutions selected from the group consisting of Q221R-V387A, D330L-I370E, D330L-D379E, D330M-S271Y, D330M-S274E, D330M-F342H, D330M-I370E, D330M-D379E, D330M-V387A, D330M-A390N, and D330M-K409N. Optionally, the modified caspase-9 polypeptide comprises the amino acid sequence as shown in SEQ ID NO: 3.

Optionally, a modified caspase-9 polypeptide provided herein has a basal activity less than 50% of a wild type caspase-9 polypeptide comprising the amino acid sequence of SEQ ID NO: 2.

In some embodiments, provided herein is a polynucleotide comprising a nucleic acid sequence encoding a modified caspase-9 polypeptide provided herein. Optionally, the polynucleotide comprises the nucleic acid sequence shown in SEQ ID NO: 11.

Also provided herein is an expression vector comprising a polynucleotide comprising a nucleic acid sequence encoding a modified caspase-9 polypeptide provided herein.

Also provided herein is a host cell containing any of the modified caspase-9 polypeptides or polynucleotides encoding a modified caspase-9 polypeptide provided herein. Optionally, the host cell is an immune cell. Optionally, the immune cell is a T cell.

In some embodiments, provided herein is a chimeric protein comprising a dimerization domain and a modified caspase-9 polypeptide, wherein the modified caspase-9 polypeptide comprises an amino acid sequence having at least 90% sequence identity to SEQ ID NO: 2, and at least one amino acid substitution, wherein the amino acid substitution is at an amino acid position selected from the group consisting of S271, S274, D330, F342, I370, D379, V387, A390, F406, and K409. Optionally, the at least one amino acid substitution is selected from the group consisting of S271Y, S274E, D330L, D330M, F342H, I370E, D379E, V387A, A390N, F406W, and K409N. Optionally, the modified caspase-9 polypeptide of the chimeric protein comprises at least two amino acid substitutions, wherein the at least two amino acid substitutions are at the amino acid positions selected from the group consisting of Q221-V387, D330-I370, D330-D379, D330-S271, D330-S274, D330-F342, D330-D379, D330-V387, D330-A390, and D330-K409. Optionally, the modified caspase-9 polypeptide of the chimeric protein comprises at least two amino acid substitutions selected from the group consisting of Q221R-V387A, D330L-I370E, D330L-D379E, D330M-S271Y, D330M-S274E, D330M-F342H, D330M-I370E, D330M-D379E, D330M-V387A, D330M-A390N, and D330M-K409N.

In some embodiments, provided herein is a chimeric protein comprising a dimerization domain and a modified caspase-9 polypeptide, wherein the modified caspase-9 polypeptide comprises an amino acid sequence having at least 70%, 80%, 90% 95%, 97%, 98%, or 99% sequence identity to SEQ ID NO: 2, and at least one amino acid substitution selected from the group consisting of S271Y, S274E, D330L, D330M, F342H, I370E, D379E, V387A, A390N, F406W, and K409N. Optionally, the modified caspase-9 polypeptide comprises at least two amino acid substitutions selected from the group consisting of Q221R-V387A, D330L-I370E, D330L-D379E, D330M-S271Y, D330M-S274E, D330M-F342H, D330M-I370E, D330M-D379E, D330M-V387A, D330M-A390N, and D330M-K409N. Optionally, the dimerization domain comprises a polypeptide selected from the group consisting of a FKBP polypeptide and a cyclophilin polypeptide. Optionally, the dimerization domain comprises an FKBP12 polypeptide. Optionally, the FKBP12 polypeptide contains the amino acid substitution F36V. Optionally, the chimeric protein comprises the amino acid sequence as shown in SEQ ID NO: 6. Optionally, the dimerization domain binds to the dimeric ligand AP1903, AP20187, dimeric FK506, or a dimeric FK506-like analog.

In some embodiments, provided herein is a chimeric protein comprising a dimerization domain and a modified caspase-9 polypeptide, wherein the modified caspase-9 polypeptide comprises an amino acid sequence having at least 90% sequence identity to SEQ ID NO: 2, and at least at least the amino acid substitutions D330M-D379E (i.e. D330M and D379E).

Optionally, a chimeric caspase 9 protein provided herein has a basal activity less than 50% of the basal activity of a chimeric protein comprising a FKBP ligand binding region and a caspase-9 polypeptide lacking the caspase activation and recruitment domain ("CARD") and having the amino acid sequence of SEQ ID NO: 2.

In some embodiments, provided herein is a polynucleotide comprising a nucleic acid sequence encoding a chimeric caspase-9 protein provided herein. Optionally, the polynucleotide comprises the nucleic acid sequence shown in SEQ ID NO: 8

Also provided herein is an expression vector comprising a polynucleotide comprising a nucleic acid sequence encoding a chimeric caspase-9 protein provided herein.

Also provided herein is a host cell containing any of the chimeric caspase 9 proteins or polynucleotides encoding a chimeric caspase 9 protein provided herein. Optionally, the host cell is an immune cell. Optionally, the immune cell is a T cell.

In some embodiments, an immune cell containing a modified caspase 9 polypeptide, a chimeric caspase 9 protein or a polynucleotide encoding a modified caspase 9 polypeptide or chimeric caspase 9 protein provided herein may further comprise a chimeric antigen receptor (CAR) or a polynucleotide encoding a CAR.

In some embodiments, provided herein is a method of modulating an engineered immune cell in a subject, the method comprising administering a dimeric ligand to a subject that has previously been administered an immune cell containing a chimeric caspase 9 protein or a polynucleotide encoding a chimeric caspase 9 protein provided herein, wherein the dimeric ligand binds to the dimerization domain of the chimeric protein, and wherein caspase-9 activity is induced upon binding of the ligand to the dimerization domain. Optionally, the ligand is AP1903.

In some embodiments, provided herein is a method of preparing an engineered immune cell, the method comprising introducing a polynucleotide encoding a modified caspase-9 polypeptide or a chimeric caspase 9 protein provide herein, or an expression vector containing the polynucleotide into the immune cell.

In some embodiments, provided herein is engineered immune cell expressing a chimeric caspase 9 protein as described herein for use as a medicament. In some embodiments, the immune cell is obtained from a healthy donor. In some embodiments, the immune cell is obtained from a patient.

In some embodiments, a method provided herein includes: providing an immune cell; introducing into the cell at least one polynucleotide encoding a modified caspase 9 polypeptide provided herein; and expressing said polynucleotide into the cell.

In some embodiments, provided herein is a method of treating a subject, the method comprising: providing an immune cell expressing a chimeric caspase-9 protein as described herein; and administering said immune cells to said patient.

In some embodiments, an immune cell used with compositions and methods provided herein can be derived from a T cell or a natural killer cell.

In some embodiments, provided herein is a pharmaceutical composition comprising a host cell containing a chimeric caspase-9 protein as described herein.

In some embodiments, the host cell is an immune cell, and the immune cell can comprise a disruption in one or more endogenous genes, wherein the endogenous gene encodes TCRα, TCRβ, CD52, glucocorticoid receptor (GR), deoxycytidine kinase (dCK), or an immune checkpoint protein such as for example programmed death-1 (PD-1).

DETAILED DESCRIPTION

Figure 1A:
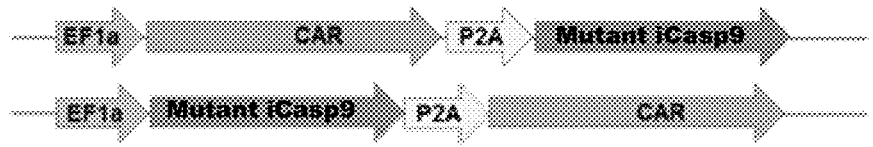
FIGS. 1A-1C is a series of schematic diagrams depicting some of the constructs provided herein; in these construct a chimeric caspase-9 protein comprising a mutant form of caspase-9 and dimerization domain is co-expressed with a CAR using either a P2A (FIG. 1A) or IRES (FIG. 1B) ribosome skip site, and a schematic of a control used to assess the extent of apoptosis is also presented (FIG. 1C).

The disclosure disclosed herein relates to modified caspase-9 polypeptides and chimeric proteins containing the modified caspase-9 polypeptides. The disclosure also provides polynucleotides encoding these caspase-9 polypeptides and chimeric proteins, and related compositions and methods of manufacture and use, such as in as in engineered host cells for administration to a subject.

General Techniques

The practice of the disclosure will employ, unless otherwise indicated, conventional techniques of molecular biology (including recombinant techniques), microbiology, cell biology, biochemistry, immunology, virology, monoclonal antibody generation and engineering, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

The terms "polypeptide", "oligopeptide", "peptide" and "protein" are used interchangeably herein to refer to chains of amino acids of any length. For example, the chain may be relatively short (e.g., 10-100 amino acids), or longer. The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this disclosure.

As used herein, "immune cell" refers to a cell of hematopoietic origin functionally involved in the initiation and/or execution of innate and/or adaptive immune response.

As used herein "autologous" means that cells, a cell line, or population of cells used for treating patients are originating from said patient or from a Human Leucocyte Antigen (HLA) compatible donor.

As used herein "allogeneic" means that cells or population of cells used for treating patients are not originating from said patient but from a donor.

An "individual" or a "subject" is a mammal, e.g., a human. Mammals also include, but are not limited to primates, horses, dogs, cats, mice and rats.

As used herein, "vector" means a construct, which is capable of delivering, and, typically expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

Reference to "about" a value or parameter herein includes (and describes) embodiments that are directed to that value or parameter per se. For example, description referring to "about X" includes description of "X." Numeric ranges are inclusive of the numbers defining the range. Generally speaking, the term "about" refers to the indicated value of the variable and to all values of the variable that are within the experimental error of the indicated value (e.g. within the 95% confidence interval for the mean) or within 10 percent of the indicated value, whichever is greater. Where the term "about" is used within the context of a time period (years, months, weeks, days etc.), the term "about" means that period of time plus or minus one amount of the next subordinate time period (e.g. about 1 year means 11-13 months; about 6 months means 6 months plus or minus 1 week; about 1 week means 6-8 days; etc.), or within 10 percent of the indicated value, whichever is greater.

It is understood that wherever embodiments are described herein with the language "comprising," otherwise analogous embodiments described in terms of "consisting of" and/or "consisting essentially of" are also provided.

Where aspects or embodiments of the disclosure are described in terms of a Markush group or other grouping of alternatives, the disclosure encompasses not only the entire group listed as a whole, but each member of the group individually and all possible subgroups of the main group, but also the main group absent one or more of the group members. The disclosure also envisages the explicit exclusion of one or more of any of the group members in the claimed invention.

Unless otherwise defined, all technical and scientific terms used herein have the same meaning as commonly understood by one of ordinary skill in the art to which this disclosure belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Exemplary methods and materials are described herein, although methods and materials similar or equivalent to those described herein can also be used in the practice or testing of the disclosure. The materials, methods, and examples are illustrative only and not intended to be limiting.

Modified Caspase-9 Polypeptides

The disclosure provided herein relates to modified caspase-9 polypeptides. As used herein, a "caspase-9 polypeptide" refers to a polypeptide that contains the amino acid sequence of wild-type human caspase-9 (i.e. SEQ ID NO: 1), a polypeptide that contains a portion of the amino acid sequence of wild-type human caspase-9, wherein the portion can induce caspase-9 mediated signaling (e.g. human caspase-9 without the caspase activation and recruitment ("CARD") domain, which has an amino acid sequence as shown in SEQ ID NO: 2), or a polypeptide having at least 60%, 65%, 70%, 75%, 80%, 85%, 90%, 95%, 96%, 97%, 98%, or 99% sequence identity to amino acid sequence as shown in SEQ ID NO: 1 or 2. As used herein, a "modified caspase-9 polypeptide" refers to a caspase-9 polypeptide as described above, wherein the polypeptide has at least 1 amino acid mutation as compared to the corresponding wild-type human caspase 9 polypeptide.

The amino acid sequence of wild-type human caspase 9 protein (UniProt ID #P55211) is: MDEADRRLLRR-CRLRLVEELQVDQLWDALLSRELFRPH-MIEDIQRAGSGSRRDQA RQLIIDLETRGSQALPLFIS-CLEDTGQDMLASFLRTNRQAAKLSKPTLENLTPVVL RP EIRKPEVLRPETPRPVDIGSGGEGDVGALESLRG-NADLAYILSMEPCGHCLIINNVNE CRESGLRTRTG-SNIDCEKLRRRFSSLHFMVEVKGDLTAKKMVLALLE-LAQQDHGA LDCCVVVILSHGCQASHLQFPGAVYGTDGCPVS-VEKIVNIFNGTSCPSLGGKPKLFFI QACGGEQKDHGFEVASTSPEDESPGSNPEP-DATPFQEGLRTFDQLDAISSLPTPSDIF VSYS-TFPGFVSWRDPKSGSWYVETLD-DIFEQWAHSEDLQSLLLRVANAVSVKGIYK QMPGCFNFLRKKLFFKTS (SEQ ID NO: 1). Accordingly, in some embodiments, a modified caspase-9 polypeptide provided herein contains at least 1 amino acid modification as compared to the amino acid sequence as shown in SEQ ID NO: 1.

The amino acid sequence of human caspase 9 protein without the CARD domain is: GFGDVGALESLRGNAD-LAYILSMEPCGHCLIINNVNFCRESGLRTRTG-SNIDCEKLR RRFSSLHFMVEVKGDLTAKKMVLAL-LELAQQDHGALDCCVVVILSHGCQASHLQF PGAVYGTDGCPVS-VEKIVNIFNGTSCPSLGGKPKLFFIQACGGEQKDHG FEVASTSP EDESPGSNPEPDATPFQEGLRTFDQL-DAISSLPTPSDIFVSYSTFPGFVSWRDPKSGS WYVETLDDIFEQWAHSEDLQSLLLRVA-NAVSVKGIYKQMPGCFNFLRKKLFFKTS (SEQ ID NO: 2). Accordingly, in some embodiments, a modified caspase-9 polypeptide provided herein contains at least 1 amino acid modification as compared to the amino acid sequence as shown in SEQ ID NO: 2.

The polypeptide of SEQ ID NO: 2 is the same as that of SEQ ID NO: 1, except that the polypeptide of SEQ ID NO: 2 does not contain amino acids 1-134 of SEQ ID NO: 1 (i.e. the CARD domain of wild-type caspase 9). Thus, the first amino acid of SEQ ID NO: 2 is the same as amino acid #135 of SEQ ID NO: 1.

In some embodiments, provided herein is a modified caspase 9 polypeptide containing at least one amino acid substitution, wherein the amino acid substitution is at an amino acid position selected from the group consisting of S271, S274, D330, F342, I370, D379, V387, A390, F406, and K409. The amino acid substitution at the listed positions may be conservative or non-conservative. The modified caspase 9 polypeptide may have at least 60%, 65%, 70%, 75%, 80%, 85%, 90%, 95%, 96%, 97%, 98%, or 99% sequence identity to an amino acid sequence as shown in SEQ ID NO: 1 or 2.

In some embodiments, provided herein is a modified caspase 9 polypeptide containing at least 1 of the following amino acid substitutions: S271Y, S274E, D330L, D330M, F342H, I370E, D379E, V387A, A390N, F406W, or K409N. In some embodiments, provided herein is a modified caspase 9 polypeptide containing at least 1 of the following amino acid substitutions: S271Y, S274E, D330L, D330M, F342H, I370E, D379E, V387A, A390N, F406W, or K409N, wherein the modified caspase 9 polypeptide has at least 60%, 65%, 70%, 75%, 80%, 85%, 90%, 95%, 96%, 97%, 98%, or 99% sequence identity to an amino acid sequence as shown in SEQ ID NO: 1 or 2.

In some embodiments, provided herein is a modified caspase 9 polypeptide containing at least two amino acid substitutions, wherein the amino acid substitutions are at the amino acid positions selected from the group consisting of Q221-V387, D330-I370, D330-D379, D330-S271, D330-S274, D330-F342, D330-I370, D330-D379, D330-V387, D330-A390, and D330-K409. The amino acid substitutions at the listed positions may be conservative or non-conservative. The modified caspase 9 polypeptide may have at least 60%, 65%, 70%, 75%, 80%, 85%, 90%, 95%, 96%, 97%, 98%, or 99% sequence identity to an amino acid sequence as shown in SEQ ID NO: 1 or 2.

In some embodiments, a modified caspase-9 polypeptide provided herein contains at least 2 amino acid substitutions. In some embodiments, provided herein is a modified caspase 9 polypeptide containing at least two amino acid substitutions, wherein the two amino acid substitutions are selected from: Q221R-V387A, D330L-I370E, D330L-D379E, D330M-S271Y, D330M-S274E, D330M-F342H, D330M4370E, D330M-D379E, D330M-V387A, D330M-A390N, or D330M-K409N.

In some embodiments, provided herein is a modified caspase 9 polypeptide containing at least two amino acid substitutions, wherein the two amino acid substitutions are selected from: Q221R-V387A, D330L-I370E, D330L-D379E, D330M-S271Y, D330M-S274E, D330M-F342H, D330M-I370E, D330M-D379E, D330M-V387A, D330M-A390N, or D330M-K409N, wherein the modified caspase 9 polypeptide has at least 60%, 65%, 70%, 75%, 80%, 85%, 90%, 95%, 96%, 97%, 98%, or 99% sequence identity to an amino acid sequence as shown in SEQ ID NO: 1 or 2.

In some embodiments, a modified caspase 9 polypeptide containing at least two amino acid substitutions contains an amino acid sequence: GFGDVGALESLRGNADLAYILS-MEPCGHCLIINNVNFCRESGLRTRTGSNIDCEKLR RRFSSLHFMVEVKGDLTAKKMVLALLE-LAQQDHGALDCCVVVILSHGCQASHLQF PGAVYGTDGCPVS-VEKIVNIFNGTSCPSLGGKPKLFFIQACGGEQKDHG FEVASTSP EDESPGSNPEPDATPFQEGLRTFDQL-MAISSLPTPSDIFVSYSTFPGFVSWRDPKSGS WYVETLDDIFEQWAHSEELQSLLLRVA-NAVSVKGIYKQMPGCFNFLRKKLFFKTS (SEQ ID NO: 3). SEQ ID NO: 3 is the sequence of SEQ ID NO: 2, with the D330M and D379E substitutions; these substitutions are underlined in the SEQ ID NO: 3 above.

In some embodiments, provided herein is a modified caspase 9 polypeptide containing any of the amino acid substitutions described in Example 1 herein. In some embodiments, provided herein is a modified caspase 9 polypeptide containing an amino acid substitution at any 1, 2, 3, 4, or 5 of the substitution positions described in Example 1 herein. In some embodiments, provided herein is a modified caspase 9 polypeptide containing any of the amino acid substitutions described in Example 1 or an amino acid substitution at any 1, 2, 3, 4, or 5 of the substitution positions described in Example 1, wherein the modified caspase 9 polypeptide has at least 60%, 65%, 70%, 75%, 80%, 85%, 90%, 95%, 96%, 97%, 98 or 99% sequence identity to an amino acid sequence as shown in SEQ ID NO: 1 or 2.

For clarity, amino acid substitutions referred to herein are annotated as follows. In a substitution described as, for example, "D379E", the "D" refers to the amino acid in the wild-type caspase 9 protein at amino acid position 379 (i.e. the 379$^{th}$ amino acid in the wild-type caspase 9 amino acid sequence, in the N-terminus to C-terminus direction), and the "E" refers to the amino acid substituted in place of the "D". Also all caspase-9 amino acid substitutions referred to herein are described in reference to the position of the respective amino acid in the full-length, wild-type caspase 9 polypeptide (i.e. to the amino acid position in SEQ ID NO: 1). Thus, for example, the substitution "D379E" refers to the same amino acid substitution in both SEQ ID NO: 1 and SEQ ID NO: 2 (even though the sequence of SEQ ID NO: 2 is shorter than the sequence of SEQ ID NO: 1).

As used herein "caspase-9 activity" refers to one or more effects in a cell which are mediated by caspase-9 (e.g. caspase-9-dependent cell-signaling events, induction of apoptosis, cell death, etc.) Caspase-9 activity may be assayed directly (e.g. by directly assaying for caspase-9-mediated cleavage of caspase-9 targets such as pro-casepase-3 or procaspase-7), or caspase-9 activity may be assayed by further downstream caspase-9 mediated events in a cell (e.g. apoptosis or cell death). For example, in some embodiments, caspase-9 activity may be assayed as described in Example 1 herein. Caspase-9 activity may also be assayed, for example, by methods known in the art for assaying caspase activity, such as a Caspase-Glo® assay (Promega), an Annexin V assay, or a secreted alkaline phosphatase (SEAP) assay (see e.g. MacCorkle, R. A., K. W. Freeman, and D. M. Spencer, Synthetic activation of Caspases: artificial death switches. Proc Natl Acad Sci USA, 1998. 95(7): p. 3655-60). See also, for example, Example 8 of U.S. Pat. No. 9,434,935.

In some embodiments, a modified caspase-9 polypeptide provided herein may have less basal caspase 9 activity than a corresponding wild-type caspase-9 polypeptide. As used herein, "basal caspase-9 activity", "basal activity" or the like refers to the activity of caspase-9 polypeptide in the absence of a specific caspase-9 inducing factor (e.g. for chimeric caspase-9 proteins provided herein, basal activity refers to the caspase-9 activity of the chimeric caspase-9 protein in the absence of the corresponding dimeric ligand). In some embodiments, a modified caspase-9 polypeptide may have less than 50%, 40%, 30%, 20%, 10%, 5%, 3%, 2%, or 1% of the basal caspase-9 activity than a corresponding wild-type caspase 9 polypeptide. Basal activity of a caspase-9 polypeptide may be assayed by methods known in the art for assaying caspase activity, such as methods as described above and in Example 1 herein.

In some embodiments, provided herein are modified caspase-9 polypeptides having 1 or 2 of the amino acid substitutions described above, and further comprising one or more additional amino acid substitutions, additions, or deletions which do not significantly affect the property of the respective caspase-9 polypeptide. In embodiments, the change may be one or more conservative amino acid substitutions, as shown in Table 1. Amino acid sequence insertions include amino- and/or carboxyl-terminal fusions ranging in length from one residue to polypeptides containing a hundred or more residues, as well as intrasequence insertions of single or multiple amino acid residues. In some embodiments, provided herein are modified caspase-9 polypeptides having 1 or 2 of the amino acid substitutions described above, and further comprising one or more additional amino acid substitutions, additions, or deletions, wherein the one or more additional amino acid substitutions, additions, or deletions improve one or more properties of the respective caspase-9 polypeptide.

TABLE 1

Amino Acid Substitutions

| Original Residue (naturally occurring amino acid) | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met Ala; Phe; Norleucine |
| Leu (L) | Ile | Norleucine; Ile; Val; Met Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Chimeric Caspase-9 Proteins

In some embodiments, provided herein is an engineered chimeric protein containing at least two components: 1) a modified caspase-9 polypeptide and 2) a dimerization domain. Chimeric proteins containing these two components may also be referred to herein as "chimeric caspase-9 proteins".

In some embodiments, in a chimeric caspase-9 protein, the dimerization domain is N-terminal to the modified-caspase-9 polypeptide. Optionally, a linker region can be present in a chimeric caspase-9 protein between the dimerization domain and the modified caspase-9 polypeptide. Optionally, a chimeric caspase-9 protein may contain at least the following components, in N-terminal to C-terminal direction: dimerization domain—linker region—modified caspase-9 polypeptide.

Chimeric Caspase 9 Protein: Caspase-9 Polypeptide Portion

The caspase-9 polypeptide portion of a chimeric caspase-9 protein may have any of the characteristics provided above for a modified caspase-9 polypeptide.

For example, in some embodiments, the caspase-9 polypeptide of a chimeric caspase-9 protein may contain at least 1 of the following amino acid substitutions: S271Y, S274E, D330L, D330M, F342H, I370E, D379E, V387A, A390N, F406W, or K409N, wherein the modified caspase 9 polypeptide has at least 60%, 65%, 70%, 75%, 80%, 85%, 90%, 95%, 96%, 97%, 98%, or 99% sequence identity to an amino acid sequence as shown in SEQ ID NO: 1 or 2. In another example, in some embodiments, the caspase-9 polypeptide of a chimeric caspase-9 protein may contain at least two amino acid substitutions, wherein the two amino acid substitutions are selected from: Q221R-V387A, D330L-I370E, D330L-D379E, D330M-S271Y, D330M-S274E, D330M-F342H, D330M-I370E, D330M-D379E, D330M-V387A, D330M-A390N, or D330M-K409N, wherein the modified caspase 9 polypeptide has at least 60%, 65%, 70%, 75%, 80%, 85%, 90%, 95%, 96%, 97%, 98%, or 99% sequence identity to an amino acid sequence as shown in SEQ ID NO: 1 or 2. In another example, in some embodiments, the caspase-9 polypeptide of a chimeric caspase-9 protein may contain at least one amino acid substitution, wherein the amino acid substitution is at an amino acid position selected from the group consisting of S271, S274, D330, F342, I370, D379, V387, A390, F406, and K409, wherein the modified caspase 9 polypeptide has at least 60%, 65%, 70%, 75%, 80%, 85%, 90%, 95%, 96%, 97%, 98%, or 99% sequence identity to an amino acid sequence as shown in SEQ ID NO: 1 or 2. In another example, in some embodiments, the caspase-9 polypeptide of a chimeric caspase-9 protein may contain at least two amino acid substitutions at the amino acid positions selected from the group consisting of Q221-V387, D330-I370, D330-D379, D330-S271, D330-S274, D330-F342, D330-I370, D330-D379, D330-V387, D330-A390, and D330-K409, wherein the modified caspase 9 polypeptide has at least 60%, 65%, 70%, 75%, 80%, 85%, 90%, 95%, 96%, 97%, 98%, or 99% sequence identity to an amino acid sequence as shown in SEQ ID NO: 1 or 2.

Chimeric Caspase 9 Protein: Dimerization Domain

The "dimerization domain" of a chimeric caspase-9 protein may be any amino acid sequence that can be induced to dimerize, such as by a dimeric ligand that can bind to the dimerization domain. For example, the dimerization domain may contain the amino acid sequence of an FK506 Binding Protein ("FKBP"). The protein FKBP proteins specifically bind to the drug FK506. Ligands that are multimeric analogs of FK506 (i.e. ligands which contain at least two copies of FK506, or derivatives thereof) can induce the dimerization of a first protein and second protein that each contain the amino acid sequence of an FKBP, by the ligand binding to both the first protein and second protein, and thereby bringing them together. Thus, chimeric caspase-9 proteins provided herein may be induced to dimerize by exposure of the chimeric caspase-9 protein to a suitable dimeric ligand which binds to the dimerization domain of the chimeric caspase-9 protein.

In some embodiments, dimerization domains of chimeric caspase-9 proteins provided herein may contain amino acid sequences of or derived from, for example, FKBPs, cyclophilins, steroid binding proteins, estrogen binding proteins, glucocorticoid binding proteins, vitamin D binding proteins, or tetracycline binding proteins. As used herein, an "FKBP polypeptide", "cyclophilin polypeptide" or like refers to a polypeptide having the amino acid sequence of the respective protein, or a portion thereof or variant thereof, wherein the portion or variant thereof retains the ability to bind to the corresponding ligand (e.g. for a FKBP polypeptide, the ligand FK506 and related molecules) with high affinity.

In some embodiments, the dimerization domain may contain an FKBP polypeptide amino acid sequence. FKBPs are a group of proteins that have prolyl isomerase activity and bind to the drug FK506 and other related drugs. Optionally, the FKBP may be human FKBP12 (also known as FKBP1A; GenBank: CAG46965.1). Optionally, a FKBP12 polypeptide may contain the F36V mutation. FKBP12 containing the F36V mutation binds with high affinity to the dimeric ligand AP1903 (Jemal, A. et al., CA Cancer J. Clinic. 58, 71-96 (2008); Scher, H. I. and Kelly, W. K., Journal of Clinical Oncology 11, 1566-72 (1993)). In addition, FKBP12 containing the F36V mutation binds to AP1903 with much higher affinity than wild-type FKBP12 binds AP1903.

An exemplary dimerization domain amino acid sequence (containing an FKBP12 polypeptide with the F36V mutation) is:

(SEQ ID NO: 4)
GVQVETISPGDGRTFPKRGQTCVVHYTGMLEDGKKVDSSRDRNKPFK

FMLGKQEVIRGWEEGVAQMSVGQRAKLTISPDYAYGATGHPGIIPPH

ATLVFDVELLKLES.

In some embodiments, a dimerization domain may be cyclophilin polypeptide amino acid sequence. Cyclophilins are proteins that bind to ciclosporin (cyclosporin A). Cyclophilins include, for example, cyclophilin A and cyclophilin D.

In some embodiments, a dimerization domain may be at least about 25, 50, 75, or 100, and no more than about 150, 200, 250, 300, 350, or 400 amino acids in length. In some embodiments, a dimerization domain may have any of the characteristics of the ligand binding region disclosed in U.S. Pat. No. 9,434,935, which is hereby incorporated by reference for all purposes.

Chimeric Caspase 9 Protein: Linker Region

In some embodiments a linker region for a chimeric caspase 9 protein is between about 5 and 100 amino acids in length. Optionally, the linker region can be between about 5 and 20 amino acids in length. The linker region is typically flexible and glycine-rich. In some embodiments, the linker region can have the amino acid sequence of GGGSGVD (SEQ ID NO: 5), (GGGGS)x (SEQ ID NO: 12) where x is an integer between 1 and 5 and (GGGS)x (SEQ ID NO: 13) where x is an integer between 1 and 5, GST-SGSGKPGSGEGSTKG (SEQ ID NO: 14), GGGGSGGGGSGGGGS (SEQ ID NO: 15), xxxGKPGSGExxxGKPGSGExxx, wherein x is any amino acid (SEQ ID NO: 16), KPGSGE (SEQ ID NO: 17), GKPGSGE (SEQ ID NO: 18), GKPGSGG (SEQ ID NO: 19), GGGSGKPGSGEGGGS (SEQ ID NO: 20), GGGGSGKPGSGEGGGGS (SEQ ID NO: 21), GGGGSGKPGSGGGGS (SEQ ID NO: 22), GGGGSGKPGSGEGGS (SEQ ID NO: 23), GGGGSGKPGSGEGGGS (SEQ ID NO: 24), GGGGSGKPGSGEGGGGS (SEQ ID NO: 25), GSGKPGSGEG (SEQ ID NO: 26), GKPGSGEG (SEQ ID NO: 27), SGKPGSGE (SEQ ID NO: 28), KPGSG (SEQ ID NO: 29), STSGSGKPGSGEGST (SEQ ID NO: 30), GGGGSGGGGSGGGGSG (SEQ ID NO: 31), GGGGGSGGGGSGGGGS (SEQ ID NO: 32), and GGGGSGGGGSGGGGS (SEQ ID NO: 33).

Chimeric Caspase 9 Protein: Examples

In some embodiments, a chimeric caspase-9 protein may have the following amino acid sequence: GVQVETISPGDGRTFPKRGQTCVVHYTGMLEDGKK VDSSRDRNKPFKFMLGKQEV IRGWEEGVAQMSVGQRAKLTISPDYAYGATGHPGIIP-PHATLVFDVELLKLESGGG SGVDGFGDV-GALESLRGNADLAYILSMEPCGHCLI-INNVNFCRESGLRTRTGSNIDC EKLRRRFSSLHFMVEVKGDLTAKKMVLALLE- LAQQDHGALDCCVVVILSHGCQAS HLQFP-GAVYGTDGCPVS-VEKIVNIFNGTSCPSLGGKPKLFFIQACGGEQKDHG FEVA STSPEDESPGSNPEPDATPFQEGLRTFDQL-MAISSLPTPSDIFVSYSTFPGFVSWRDPK SGSWYVETLDDIFEQWAHSEELQSLLLRVA-NAVSVKGIYKQMPGCFNFLRKKLFFK TS (SEQ ID NO: 6). In this sequence, the following components are present, in N terminus to C-terminus direction: 1) a dimerization domain, containing an FKBP12 polypeptide with the F36V mutation; 2) a linker region (the first amino acid of the linker region is underlined); and 3) a modified caspase-9 polypeptide, containing a caspase 9 polypeptide without the CARD domain, and containing D330M and D379E substitutions (the first amino acid of the modified caspase-9 polypeptide is underlined).

In some embodiments, a chimeric caspase-9 protein may be any of the chimeric caspase-9 proteins described herein in Example 1.

In some embodiments, a chimeric caspase-9 protein provided herein (i.e. which contains a modified caspase-9 polypeptide) may have less basal activity than a corresponding chimeric caspase-9 protein which contains a wild-type caspase-9 polypeptide. In some embodiments, a chimeric caspase-9 protein may have less than 50%, 40%, 30%, 20%, 10%, 5%, 3%, 2%, or 1% of the basal activity of a corresponding chimeric caspase-9 protein which contains a wild-type caspase-9 polypeptide. In some embodiments, a chimeric caspase-9 protein containing a FKBP12 dimerization domain and a modified caspase-9 polypeptide provide herein lacking the CARD domain may have less than 50%, 40%, 30%, 20%, 10%, 5%, 3%, 2%, or 1% of the basal activity of a corresponding chimeric caspase-9 protein containing a FKBP12 dimerization domain and a wild-type caspase-9 polypeptide lacking the CARD domain.

In some embodiments, a chimeric caspase-9 protein provided herein (i.e. which contains a modified caspase-9 polypeptide) may have less basal activity than a corresponding chimeric caspase-9 protein which contains a wild-type caspase-9 polypeptide, as measured by a SEAP assay, a Caspase-Glo® assay, an Annexin V assay, or the assay as provided in Example 1 herein. In some embodiments, a chimeric caspase-9 protein containing a FKBP12 dimerization domain and a modified caspase-9 polypeptide provide herein lacking the CARD domain may have less than 50%, 40%, 30%, 20%, 10%, 5%, 3%, 2%, or 1% of the basal activity of a corresponding chimeric caspase-9 protein containing a FKBP12 dimerization domain and a wild-type caspase-9 polypeptide lacking the CARD domain, as measured by a SEAP assay, a Caspase-Glo® assay, an Annexin V assay, or the assay as provided in Example 1 herein. In some embodiments, a chimeric caspase-9 protein containing a FKBP12 dimerization domain and a modified caspase-9 polypeptide provide herein lacking the CARD domain may have less than 50%, 40%, 30%, 20%, 10%, 5%, 3%, 2%, or 1% of the basal activity of a corresponding chimeric caspase-9 protein containing a FKBP12 dimerization domain and a wild-type caspase-9 polypeptide lacking the CARD domain, as measured by a SEAP assay, a Caspase-Glo® assay, an Annexin V assay, or the assay as provided in Example 1 herein, further wherein the chimeric caspase-9 protein has at least 100%, 90%, 80%, 70%, 60%, 50%, 40%, 30%, 20%, 10%, or 5% of the caspase activity in response to a dimeric ligand of the corresponding chimeric caspase-9 protein containing a FKBP12 dimerization domain and a wild-type caspase-9 polypeptide lacking the CARD domain, wherein the caspase activity is measured by a SEAP assay, a Caspase-Glo® assay, an Annexin V assay, or the assay as provided in Example 1 herein.

In some embodiments, a chimeric caspase-9 protein provided herein may have more caspase-9 activity in the presence of a corresponding dimeric ligand than in the absence of a dimeric ligand. In some embodiments, a chimeric caspase-9 protein provided herein may have at least 2× (i.e. "2 times" or "2-fold'), 3×, 5×, 10×, 20×, 50×, or 100× greater caspase-9 activity in the presence of, for example, 10 nM or 10 mM of a corresponding dimeric ligand than in the absence of the dimeric ligand. For example, in some embodiments provided herein, a chimeric caspase-9 protein contains a FKBP12 dimerization domain, wherein the FKBP12 protein further contains the F36V substitution. Continuing with this example, in some embodiments, the caspase-9 activity of the chimeric caspase-9 protein is at least 2×, 3×, 5×, 10×, 20×, 50×, or 100× greater in the presence of 10 mM AP1903 than in 0 mM AP1903.

Dimeric Ligands

In some embodiments, chimeric caspase-9 proteins provided herein may be induced to dimerize via a suitable dimeric ligand. The dimeric ligand can bind two copies of the chimeric caspase-9 protein (via the dimerization domain in both copies of the protein), and thereby induced dimerization of the chimeric caspase-9 proteins. Typically, dimeric ligands used with embodiments provided herein are small molecules of less than 3 kDa that can be easily administered to a subject.

In some embodiments, a dimerization domain is an FKBP12 polypeptide, and the corresponding dimeric ligand is AP1903, AP21087, AP1510, dimeric rapamycin, dimeric FK1012, dimeric FK506, or a dimeric FK506-like analog.

The dimeric ligands AP1903, AP21087, AP1510, dimeric FK1012, dimeric FK506, and others disclosed herein are known to those of skill in the art. For example, AP1903 (also known as rimiducid) is a synthetic molecule, with the following identifying information: CAS Index Name: 2-Piperidinecarboxylic acid, 1-[(2S)-1-oxo-2-(3,4,5-trimethoxyphenyl)butyl]-, 1,2 ethanediylbis[imino(2-oxo-2,1-ethanediyl)oxy-3,1-phenylene[(1R)-3-(3,-4-dimethoxyphenyl)propylidene]]ester, [2S [1(R*),2R*[S*[S*[1(R*),2R*]]]]]-(9Cl); CAS Registry Number: 195514-63-7; Molecular Formula: $C_{78}H_{98}N_4 O_{20}$; Molecular Weight: 1411.65.

AP1903 has much greater affinity for FKBP12 polypeptide with the F36V mutation than wild-type FKBP12. Thus, systems involving use in a subject of a recombinant protein containing FKBP12 with the F36V mutation and AP1903 permit selective targeting in the subject of the recombinant protein by AP1903. This is advantageous, because due to AP1903's low affinity for wild-type FKBP12, any possible side-effects that would result from the binding of a dimeric ligand to wild-type FKBP12 are minimized (i.e. only the FKBP12 with the F36V mutation is targeted). Use of AP1903 with FKBP12 polypeptides containing the F36V mutation is described, for example, in Jemal, A. et al., CA Cancer J. Clinic. 58, 71-96 (2008); Scher, H. I. and Kelly, W. K., Journal of Clinical Oncology 11, 1566-72 (1993). AP1903 has been tested for administration to humans (see, e.g. Iuliucci J D, et al., J Clin Pharmacol. 41: 870-9, 2001).

In some embodiments, a dimerization domain contains a cyclophilin polypeptide, and the corresponding dimeric ligand is dimeric cyclosporin A. In some embodiments, a dimerization domain is an estrogen binding polypeptide, and the corresponding dimeric ligand is dimeric estrogen. In some embodiments, a dimerization domain is a glucocorticoid binding polypeptide, and the corresponding dimeric ligand is dimeric glucocorticoid. In some embodiments, a dimerization domain is a tetracycline binding polypeptide, and the corresponding dimeric ligand is dimeric tetracycline. In some embodiments, a dimerization domain is a vitamin D binding polypeptide, and the corresponding dimeric ligand is dimeric vitamin D.

As used herein, a "dimeric" ligand may optionally contain more than 2 copies of a suitable binding molecule (i.e. the ligand may be multimeric); however, such ligands may still be considered "dimeric" as used herein, based on the ability of such ligands to dimerize corresponding binding molecules. Similarly, in some embodiments, a "dimerization domain" as provided herein may be capable of supporting multimerization (e.g. in the event that multiple copies of the dimerization domain are provided in the same molecule); however, such domains may also still be considered "dimerization domains" as used herein, based on the ability of such domains to dimerize. Typically, caspase-9 signaling can be effectively induced upon dimerization of caspase-9 molecules (i.e. trimerization or other multimerization is not required). In addition, references herein to a "ligand" are to a dimeric ligand (for example, when referring to a "ligand" which induces dimerization of a chimeric caspase-9 protein provided herein), unless the context clearly dictates otherwise.

Ligand-mediated dimerization of chimeric caspase-9 proteins provided herein results in induction of caspase-9 mediated signaling events in host cells containing the chimeric caspase-9 protein. This signaly typically results in apoptosis, and cell death.

In some embodiments, a chimeric caspase-9 protein provided herein may contain one or more dimerization features of, and may be induced to dimerize via a system or method provided in a system for chemically induced dimerization (CID). The CID system is based upon the notion that surface receptor aggregation effectively activates downstream signaling cascades. The CID system uses synthetic bivalent ligands to rapidly crosslink signaling molecules that are fused to ligand-binding domains. This system has been used to trigger the oligomerization and activation of cell surface (Spencer, D. M., et al., Science, 1993. 262: p. 1019-1024; Spencer D. M. et al., Curr Biol 1996, 6:839-847; Blau, C. A. et al., Proc Natl Acad. Sci. USA 1997, 94:3076-3081), or cytosolic proteins (Luo, Z. et al., Nature 1996, 383:181-185; MacCorkle, R. A. et al., Proc Natl Acad Sci USA 1998, 95:3655-3660), the recruitment of transcription factors to DNA elements to modulate transcription (Ho, S. N. et al., Nature 1996, 382:822-826; Rivera, V. M. et al., Nat. Med. 1996, 2:1028-1032) or the recruitment of signaling molecules to the plasma membrane to stimulate signaling (Spencer D. M. et al., Proc. Natl. Acad. Sci. USA 1995, 92:9805-9809; Holsinger, L. J. et al., Proc. Natl. Acad. Sci. USA 1995, 95:9810-9814). The CID system thus produces a conditionally controlled protein or polypeptide. In addition to this technique being inducible, it also is reversible, due to the degradation of the labile dimerizing agent or administration of a monomeric competitive inhibitor.

Polynucleotides

In some embodiments, also provided herein is a polynucleotide containing a nucleic acid sequence encoding a modified caspase-9 polypeptide or a chimeric caspase-9 protein described herein.

For example, in some embodiments, a modified caspase-9 polypeptide provided herein is encoded by the nucleic acid sequence:

(SEQ ID NO: 7)
GGATTTGGCGATGTGGGCGCCCTGGAGTCTCTGAG

AGGCAATGCCGATCTGGCCTACATCCTGAGCATGG

AGCCTTGCGGCCACTGTCTGATCATCAACAATGTG

AACTTCTGCAGGGAGTCCGGCCTGAGAACCAGGAC

AGGCTCTAATATCGACTGTGAGAAGCTGCGGAGAA

GGTTCTCTAGCCTGCACTTTATGGTGGAGGTGAAG

GGCGATCTGACCGCCAAGAAGATGGTGCTGGCCCT

GCTGGAGCTGGCCCAGCAGGACCACGGCGCCCTGG

ATTGCTGCGTGGTGGTCATCCTGTCTCACGGATGC

CAGGCCAGCCACCTGCAGTTCCCAGGAGCCGTGTA

TGGAACCGACGGATGTCCCGTGAGCGTGGAGAAGA

TCGTGAACATCTTTAATGGCACAAGCTGCCCATCC

CTGGGAGGCAAGCCAAAGCTGTTCTTTATCCAGGC

CTGTGGCGGCGAGCAGAAGGATCACGGCTTTGAGG

TGGCCAGCACCTCCCCAGAGGACGAGTCTCCTGGC

AGCAACCCAGAGCCCGATGCCACCCCTTTCCAGGA

GGGCCTGCGCACATTTGACCAGCTG<u>ATG</u>GCCATCT

CCTCTCTGCCTACCCCATCCGACATCTTCGTGTCT

TACAGCACATTCCCTGGCTTCGTGAGCTGGCGGGA

CCCCAAGTCCGGCTCTTGGTACGTGGAGACACTGG

ACGATATCTTTGAGCAGTGGGCACACAGCGAG<u>GAG</u>

CTGCAGTCCCTGCTGCTGAGAGTGGCCAACGCCGT

GTCCGTGAAGGGCATCTACAAGCAGATGCCAGGCT

GCTTCAATTTTCTGAGGAAAAAACTGTTCTTCAAA

ACTAGC.

The nucleic acid sequence of SEQ ID NO: 7 encodes a modified caspase-9 polypeptide without the CARD domain and having the substitutions D330M and D379E; the codons encoding these substitutions are underlined.

In another example, in some embodiments, a chimeric caspase-9 protein provided herein is encoded by the nucleic acid sequence: GGAGTGCAGGTCGAAACAATCT-CACCCGGCGATGGACGGACATTCCCCAAAAG AGGACAGACTTGCGTCGTGCATTATACCGG-CATGCTGGAGGACGGCAAGAAGG TGGACAGCTCCCGCGATCGGAACAAGCCCTT-CAAGTTTATGCTGGGCAAGCAG GAAGT-GATCAGGGGATGGGAGGAGGGAGTGGCACAGAT-GAGCGTGGGACAGA GGGCAAAGCTGACCATCTCCCCAGACTACG-CATATGGAGCAACAGGACACCCT GGAATCATCC-CACCTCACGCCACACTGGTGTTCGATGTG-GAGCTGCTGAAGCTG GAGTCCGGAGGAGGATCTGGAGTGGACGGAT-TGGCGATGTGGGCGCCCTGGA GTCTCT-GAGAGGCAATGCCGATCTGGCCTACATCCTGAG-CATGGAGCCTTGCGG CCACTGTCTGATCATCAACAATGT-GAACTTCTGCAGGGAGTCCGGCCTGAGAAC CAGGACAGGCTCTAATATCGACTGT- GAGAAGCTGCGGAGAAGGTTCTCTAGCCT
GCACTTTATGGTGGAGGTGAAGGGC-
GATCTGACCGCCAAGAAGATGGTGCTGG
CCCTGCTGGAGCTGGCCCAGCAGGAC-
CACGGCGCCCTGGATTGCTGCGTGGTGG
TCATCCTGTCTCACGGATGCCAGGCCAGC-
CACCTGCAGTTCCCAGGAGCCGTGT ATG-
GAACCGACGGATGTCCCGTGAGCGTGGAGAA-
GATCGTGAACATCTTTAAT
GGCACAAGCTGCCCATCCCTGGGAGGCAAGC-
CAAAGCTGTTCTTTATCCAGGCC
TGTGGCGGCGAGCAGAAGGATCACGGCTTT-
GAGGTGGCCAGCACCTCCCCAGA
GGACGAGTCTCCTGGCAGCAACCCAGAGCC-
GATGCCACCCCTTTCCAGGAGG GCCTGCGCACAT-
TTGACCAGCTGATGGCCATCTCCTCTCTGCC-
TACCCCATCCGA
CATCTTCGTGTCTTACAGCACATTCCCTGGCTTCGT-
GAGCTGGCGGGACCCCAA
GTCCGGCTCTTGGTACGTGGAGACACTGGACGA-
TATCTTTGAGCAGTGGGCACA CAGCGAG-
GAGCTGCAGTCCCTGCTGCTGAGAGTGGC-
CAACGCCGTGTCCGTGA
AGGGCATCTACAAGCAGATGCCAGGCTGCTTCAAT-
TTTCTGAGGAAAAAACTGT TCTTCAAAACTAGC
(SEQ ID NO: 8). The nucleic acid sequence of SEQ ID NO: 8 encodes a chimeric caspase-9 protein containing the follow components in N terminus to C-terminus direction: 1) a dimerization domain, containing an FKBP12 polypeptide with the F36V mutation; 2) a linker region; and 3) a modified caspase-9 polypeptide, containing a caspase 9 polypeptide without the CARD domain, and containing D330M and D379E substitutions. Also, the nucleic acid sequence of SEQ ID NO: 8 encodes the chimeric caspase-9 protein having an amino acid sequence as shown in SEQ ID NO: 6.

In another aspect, the disclosure provides compositions (such as a pharmaceutical compositions) comprising a host cells containing a modified caspase-9 polypeptide or chimeric caspase 9 protein provided herein. In some embodiments, the composition comprises a cell comprising a polynucleotide encoding any of the modified caspase-9 polypeptide or chimeric caspase 9 proteins described herein.

Expression vectors, and administration of polynucleotide compositions are further described herein.

In another aspect, the disclosure provides a method of making any of the polynucleotides described herein. Polynucleotides can be made and expressed by procedures known in the art.

Polynucleotides complementary to any such sequences are also encompassed by the disclosure. Polynucleotides may be single-stranded (coding or antisense) or double-stranded, and may be DNA or RNA molecules. Additional coding or non-coding sequences may, but need not, be present within a polynucleotide of the disclosure, and a polynucleotide may, but need not, be linked to other molecules and/or support materials.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, WI), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J., 1990, Unified Approach to Alignment and Phylogenes pp. 626-645 Methods in Enzymology vol. 183, Academic Press, Inc., San Diego, CA; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, CA; Wilbur, W. J. and Lipman, D. J., 1983, Proc. Natl. Acad. Sci. USA 80:726-730.

Generally, the percentage sequence identity is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

The polynucleotides of this disclosure can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the disclosure. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator), such that polynucleotide in the vector may be transcribed. For example, an expression vector comprising a polynucleotide comprising a nucleic acid encoding a chimeric caspase-9 protein or modified caspase-9 polypeptide provided herein may have a promoter which induces transcription of the nucleic acid in a host cell. For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

A polynucleotide encoding a modified caspase-9 polypeptide or chimeric caspase-9 protein disclosed herein may exist in an expression cassette or expression vector (e.g., a plasmid for introduction into a bacterial host cell, or a viral vector such as a baculovirus vector for transfection of an insect host cell, or a plasmid or viral vector such as a lentivirus for transfection of a mammalian host cell). In some embodiments, a polynucleotide or vector can include a nucleic acid sequence encoding ribosomal skip sequences such as, for example without limitation, a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see (Donnelly and Elliott 2001; Atkins, Wills et al. 2007; Doronina, Wu et al. 2008)). By "codon" is meant three nucleotides on an mRNA (or on the sense strand of a DNA molecule) that are translated by a ribosome into one amino acid residue. Thus, two polypeptides can be synthesized from a single, contiguous open reading frame within an imRNA when the polypeptides are separated by a 2A oligopeptide sequence that is in frame. Such ribosomal skip mechanisms are well known in the art and are known to be used by several vectors for the expression of several proteins encoded by a single messenger RNA.

To direct transmembrane polypeptides into the secretory pathway of a host cell, in some embodiments, a secretory signal sequence (also known as a signal peptide, leader sequence, prepro sequence or pre sequence) is provided in a polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830). Those skilled in the art will recognize that, in view of the degeneracy of the genetic code, considerable sequence variation is possible among these polynucleotide molecules. In some embodiments, nucleic acid sequences of the disclosure are codon-optimized for expression in mammalian cells, e.g. for expression in human cells. Codon-optimization refers to the exchange in a sequence of interest of codons that are generally rare in highly expressed genes of a given species by codons that are generally frequent in highly expressed genes of such species, such codons encoding identical amino acids as the codons that are being exchanged.

Methods of Engineering a Host Cell

In some embodiments, methods of preparing host cells are provided herein.

In some embodiments, the methods comprise introducing a polynucleotide comprising a nucleic acid sequence encoding a modified caspase-9 polypeptide or chimeric caspase 9 protein provided herein into the host cell. Optionally, the method may further include expanding the cells.

In some embodiments, the host cell is an immune cell. In some embodiments, the immune cell is a T cell. In some embodiments, an immune cell can be derived from, for example without limitation, a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. The isolated cell can also be a dendritic cell, killer dendritic cell, a mast cell, a NK-cell, a B-cell or a T cell selected from the group consisting of inflammatory T-lymphocytes, cytotoxic T-lymphocytes, regulatory T-lymphocytes, memory T-lymphocytes, or helper T-lymphocytes. In some embodiments, the cell can be derived from the group consisting of CD4+ T-lymphocytes and CD8+ T-lymphocytes.

In some embodiments, a host cell into which a polynucleotide containing a nucleic acid sequence encoding a chimeric caspase 9 protein is introduced may additionally contain a polynucleotide containing a nucleic acid encoding a chimeric antigen receptor (CAR). Alternatively, in some embodiments, after a nucleic acid sequence encoding a modified chimeric caspase 9 protein is introduced into the host cell, a polynucleotide containing a nucleic acid encoding a CAR may be introduced into the cell. In both of the above embodiments, a host cell containing both a chimeric caspase 9 protein and a CAR is generated. As described elsewhere herein, it can be desirable to engineer immune cells that contain, for example, a CAR to additionally contain a chimeric caspase 9 protein as provided herein, to permit the induction of apoptosis in these cells, if needed.

Methods for engineering immune cells and preparing CAR T cells are described in, for example, PCT Patent Application Publication Nos. WO/2014/039523, WO/2014/184741, WO/2014/191128, WO/2014/184744, and WO/2014/184143, each of which is incorporated herein by reference in its entirety. Also, in some embodiments, CARs and CAR T cells containing a CAR and a modified caspase-9 polypeptide or a chimeric caspase-9 protein as provided herein may be generally prepared as provided, for example, in Jackson et al, Nature Reviews Clinical Oncology, 13, 370-383 (2016); Maus et al, Blood, 123, 2625-2635 (2014); Dai et al, Journal of the National Cancer Institute, Vol 8, No. 7 (2016); Wang & Riviere, Molecular Therapy—Oncolytics, 3, 16015 (2016); Liechtenstein et al, Cancers (Basel), 5(3), 815-837 (2013), and in references provided therein. In some embodiments, a modified caspase-9 polypeptide or chimeric caspase-9 protein and CAR-containing immune cell provided herein may have any of the features and may be prepared by any of the methods described for CARs and CAR-containing immune cells provided in U.S. patent application Ser. No. 15/085,317, filed Mar. 30, 2016, which is hereby incorporated by reference for all purposes.

In some embodiments, a method provided herein comprises: transforming an immune cell with: i) at least one polynucleotide encoding a chimeric caspase 9 protein as provided herein, at least one polynucleotide encoding a CAR, and ii) expressing the polynucleotides in the cell.

Methods and techniques for introducing a polynucleotide containing a nucleic acid sequence encoding a CAR may also be used to introduce a polynucleotide containing a nucleic acid sequence encoding a chimeric caspase 9 protein. In some embodiments, a polynucleotide encoding a chimeric caspase 9 protein may be present in lentiviral vectors for stable expression in the cells.

In some embodiments, a method for engineering a host cell with a polynucleotide encoding a modified caspase 9 polypeptide or chimeric caspase 9 protein can further comprise a step of genetically modifying the host cell by inactivating at least one gene expressing, for example without limitation, a component of the TCR, a target for an immunosuppressive agent, an HLA gene, and/or an immune checkpoint protein such as, for example, PDCD1 or CTLA-4. By inactivating a gene it is intended that the gene of interest is not expressed in a functional protein form. In some embodiments, the gene to be inactivated is selected from the group consisting of, for example without limitation, TCRα, TCRβ, dCK, CD52, GR, PD-1, and CTLA-4. In some embodiments the method comprises inactivating one or more genes by introducing into the cells a rare-cutting endonuclease able to selectively inactivate a gene by selective DNA cleavage. In some embodiments the rare-cutting endonuclease can be, for example, a transcription activator-like effector nuclease (TALE-nuclease) or Cas9 endonuclease.

In some embodiments, polynucleotides encoding polypeptides according to the present disclosure can be mRNA which is introduced directly into the cells, for example by electroporation. In some embodiments, cytoPulse technology can be used to transiently permeabilize living cells for delivery of material into the cells. Parameters can be modified in order to determine conditions for high transfection efficiency with minimal mortality.

Engineered Host Cells

The disclosure also provides engineered host cells comprising a polynucleotide encoding any of the modified caspase-9 polypeptides or chimeric caspase-9 proteins provided herein. In some embodiments, a polynucleotide encoding a caspase-9 protein provided herein can be introduced into an host cell as a transgene via a plasmid vector. In some embodiments, the plasmid vector can also contain, for example, a selection marker which provides for identification and/or selection of cells which received the vector. Typically, a host cell provided herein is an immune cell, for example a primary T cell (see, e.g., FIGS. 4-9), although other types of host cells are also possible.

When a chimeric caspase-9 protein provided herein is expressed in a host cell, typically, the chimeric caspase-9 protein is oriented such that the dimerization domain is extracellular (and thus readily able to interact with dimeric ligands), and wherein at least a portion of the caspase-9 polypeptide of the protein is intracellular (and thus able to readily mediate intracellular caspase-9 signaling pathways).

Modified caspase-9 polypeptides may be synthesized in situ in the cell after introduction of polynucleotides encoding the modified caspase-9 polypeptides into the cell. Alternatively, modified caspase-9 polypeptides may be produced outside of cells, and then introduced into cells. Methods for introducing a polynucleotide construct into cells are known in the art. In some embodiments, stable transfection methods can be used to integrate the polynucleotide construct into the genome of the cell. In other embodiments, transient transfection methods can be used to transiently express the polynucleotide construct, and the polynucleotide construct is not integrated into the genome of the cell. In other embodiments, virus-mediated methods can be used. The polynucleotides may be introduced into a cell by any suitable means such as for example, recombinant viral vectors (e.g. retroviruses, adenoviruses), liposomes, and the like. Transient transfection methods include, for example without limitation, microinjection, electroporation or particle bombardment. Polynucleotides may be included in vectors, such as for example plasmid vectors or viral vectors.

Also provided herein are isolated cells and cell lines obtained by the above-described methods of engineering cells provided herein. In some embodiments, an isolated cell comprises at least one modified caspase-9 polypeptide or chimeric caspase-9 protein as described herein. Also provided herein are isolated immune cells obtained according to any one of the methods described above.

Prior to expansion and genetic modification, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available and known to those skilled in the art, may be used. In some embodiments, cells can be derived from a healthy donor, from a patient diagnosed with cancer or from a patient diagnosed with an infection. In some embodiments, cells can be part of a mixed population of cells which present different phenotypic characteristics.

Also provided herein are cell lines obtained from a transfected immune cell according to any of the above-described methods.

Figure 1B:
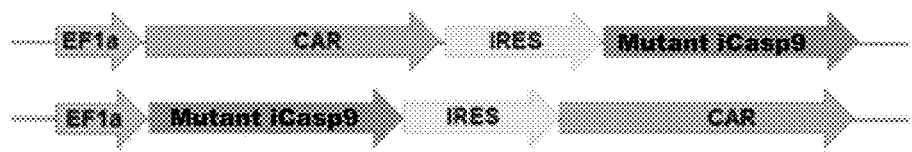
Figure 1C:
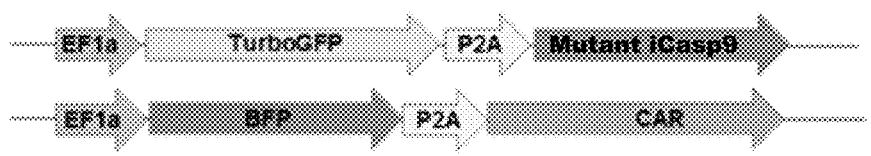

In some embodiments, an isolated cell according to the disclosure comprises a polynucleotide encoding a chimeric caspase 9 protein provided herein and a polynucleotide encoding a CAR, for example as schematically depicted in FIGS. 1A-1C.

Immune cells for use with compositions and methods provided herein can be activated and expanded, either prior to or after genetic modification of the cells, using methods as generally described, for example without limitation, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo. Generally, T cells can be expanded, for example, by contact with an agent that stimulates a CD3 TCR complex and a co-stimulatory molecule on the surface of the T cells to create an activation signal for the T cell. For example, chemicals such as calcium ionophore A23187, phorbol 12-myristate 13-acetate (PMA), or mitogenic lectins like phytohemagglutinin (PHA) can be used to create an activation signal for the T cell.

In some embodiments, the cells of the disclosure can be expanded by co-culturing with tissue or cells. The cells can also be expanded in vivo, for example in the subject's blood after administering the cell into the subject.

In some embodiments, TCR is rendered not functional in host T cells provided herein by inactivating TCRα gene and/or TCRβ gene(s) in the host cells.

Therapeutic Applications

In some embodiments, host cells containing a polynucleotide encoding a chimeric caspase-9 protein or modified caspase-9 polypeptide provided herein may be used introduced into a subject for a therapeutic purpose. For example, the host cells may be immune cells, and the immune cells (e.g. CAR T cells) may be introduced into the subject to treat a cancer in the subject. By incorporating a polynucleotide encoding a chimeric caspase-9 protein provided herein into the host cells prior to administration of the host cells to the subject, the host cells can then be modulated in the subject (if needed), according to systems and methods provided herein. For example, if it is necessary or desirable to induce apoptosis in host cells containing a chimeric caspase-9 protein provided herein after the introduction of the host cells into the subject, the subject can be administered a suitable dimeric ligand that binds to the dimerization domain in the chimeric caspase-9 protein in the host cells. The decision to eliminate the transferred cells may arise from undesirable effects being detected in the patient which are attributable to the transferred cells, such as for example, when unacceptable levels of toxicity are detected or if the cells are proliferating in an undesired manner. For example, after a subject is administered a host cell containing a chimeric caspase-9 protein provided herein, in some embodiments, the subject may be administered a corresponding dimeric ligand within 2, 4, 8, 12, 16, 24, 36, 48, 72, 96,120, or 144 hours of administration of the host cells to the subject.

In some embodiments, host cells containing a polynucleotide encoding a chimeric caspase-9 protein described herein, or cell lines derived from such cells, can be used as a medicament. In some embodiments, such a medicament can be used for treating cancer, including solid tumors and liquid tumors.

In some embodiments, a host cell provided herein used for a therapeutic purpose may contain a FKBP12 with the F36V mutation dimerization domain. To modulate such host cells in a subject, AP1903 may be administered to the subject. AP1903 may be administered to a subject according to various regimens. For example, optionally, a subject may be administered AP1903 via injection at an amount of 0.4 mg/kg, via IV infusion over a 2 hour period. AP1903 has been studied in humans (see, e.g. Iuliucci J D, et al., J Clin Pharmacol. 41: 870-9, 2001), and is well-tolerated up to doses of at least 1 mg/kg. Optionally, AP1903 may be administered to a subject to achieve a concentration of AP1903 in the subject's bloodstream in the range of, for example, about 10-100 nM, 100-1000 nM, or 1-100 mM.

Methods of treatment of the disclosure can be ameliorating, curative or prophylactic. Compositions and methods provided herein may be either part of an autologous immunotherapy or part of an allogenic immunotherapy treatment, as it may be desirable or needed (in some circumstances) to induce apoptosis in both autologous and allogenic host cells in a subject.

Cells that can be used with the methods provided herein are described, for example, in the previous section. Treatment can be used to treat patients diagnosed with, for example, cancer, or any other disorder for which it is desirable to introduce a therapeutic host cell into the subject. Host cells may be administered to a subject by any convenient manner, such as intravenously.

Kits

The disclosure also provides kits for use in the instant methods. Kits of the disclosure include one or more containers comprising i) a polynucleotide encoding a modified caspase-9 polypeptide or chimeric caspase-9 protein, or an engineered immune cell comprising a polynucleotide encoding a modified caspase-9 polypeptide or chimeric caspase-9 protein as described herein, and ii) instructions for use in accordance with any of the methods of the disclosure described herein. Generally, these instructions comprise a description of administration of an engineered immune cell for the above described therapeutic treatments. Optionally, the kit may further include a suitable dimeric ligand which binds to the dimerization domain of the chimeric caspase 9 protein, such as AP1903, and instructions including, for example, if and when to administer the dimeric ligand to a subject in need thereof.

The instructions relating to the use of the engineered immune cells and dimeric ligands as described herein generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert (e.g., a paper sheet included in the kit), but machine-readable instructions (e.g., instructions carried on a magnetic or optical storage disk) are also acceptable.

The kits of this disclosure are in suitable packaging. Suitable packaging includes, but is not limited to, vials, bottles, jars, flexible packaging (e.g., sealed Mylar or plastic bags), and the like. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle).

Kits may optionally provide additional components such as buffers and interpretive information. Normally, the kit comprises a container and a label or package insert(s) on or associated with the container.

Illustrative Embodiments

The disclosure and inventions described herein may be defined by reference to the following numbered, illustrative embodiments.

1. A modified caspase-9 polypeptide comprising an amino acid sequence having at least 90% sequence identity to SEQ ID NO: 2, and at least one amino acid substitution, wherein the amino acid substitution is at an amino acid position selected from the group consisting of S271, S274, C287, D330, F342, I370, D379, V387, A390, F406, and K409.

2. The modified caspase-9 polypeptide of claim 1, wherein the at least one amino acid substitution is selected from the group consisting of S271Y, S274E, D330L, D330M, F342H, I370E, D379E, V387A, A390N, F406W, and K409N.

3. The modified caspase-9 polypeptide of embodiment 1, wherein the polypeptide comprises at least two amino acid substitutions, wherein the at least two amino acid substitutions are at the amino acid positions selected from the group consisting of Q221-V387, D330-I370, D330-D379, D330-S271, D330-S274, D330-F342, D330-D379, D330-V387, D330-A390, and D330-K409.

4. The modified caspase-9 polypeptide of embodiment 1, wherein the polypeptide comprises at least two amino acid substitutions selected from the group consisting of Q221R-V387A, D330L-I370E, D330L-D379E, D330M-S271Y, D330M-S274E, D330M-F342H, D330M-I370E, D330M-D379E, D330M-V387A, D330M-A390N, and D330M-K409N.

5. The modified caspase-9 polypeptide of any one of embodiments 1-4, wherein the polypeptide comprises the amino acid sequence as shown in SEQ ID NO: 3

6. A polynucleotide comprising a nucleic acid sequence encoding the modified caspase-9 polypeptide of any one of embodiments 1-5.

7. The polynucleotide of embodiment 5, wherein the polynucleotide comprises the nucleic acid sequence shown in SEQ ID NO: 11

8. An expression vector comprising the polynucleotide of embodiment 6 or 7.

9. An engineered immune cell comprising the modified caspase-9 polypeptide of any one of embodiments 1-5 or the polynucleotide of embodiment 6 or 7.

10. A chimeric protein comprising a dimerization domain and a modified caspase-9 polypeptide, wherein the modified caspase-9 polypeptide comprises an amino acid sequence having at least 90% sequence identity to SEQ ID NO: 2, and at least one amino acid substitution, wherein the amino acid substitution is at an amino acid position selected from the group consisting of S271, S274, D330, F342, I370, D379, V387, A390, F406, and K409.

11. The chimeric protein of embodiment 10, wherein the at least one amino acid substitution is selected from the group consisting of S271Y, S274E, D330L, D330M, F342H, I370E, D379E, V387A, A390N, F406W, and K409N.

12. The chimeric protein of embodiment 10, wherein the modified caspase-9 polypeptide comprises at least two amino acid substitutions, wherein the at least two amino acid substitutions are at the amino acid positions selected from the group consisting of Q221-V387, D330-I370, D330-D379, D330-S271, D330-S274, D330-F342, D330-D379, D330-V387, D330-A390, and D330-K409.

13. The chimeric protein of embodiment 10, wherein the modified caspase-9 polypeptide comprises at least two amino acid substitutions selected from the group consisting of Q221R-V387A, D330L-I370E, D330L-D379E, D330M-S271Y, D330M-S274E, D330M-F342H, D330M-I370E, D330M-D379E, D330M-V387A, D330M-A390N, and D330M-K409N.

14. The chimeric protein of embodiment of any one of embodiments 10-13, wherein the dimerization domain comprises a polypeptide selected from the group consisting of a FKBP polypeptide and a cyclophilin polypeptide.

15. The chimeric protein of any one of embodiments 10-14, wherein the dimerization domain comprises an FKBP12 polypeptide.

16. The chimeric protein of embodiment 15, wherein the FKBP12 polypeptide contains the amino acid substitution F36V.

17. The chimeric protein of any one of embodiments 10-16, wherein the chimeric protein comprises the amino acid sequence as shown in SEQ ID NO: 6.

18. The chimeric protein of any one of embodiments 10-17, wherein the dimerization domain binds to the dimeric ligand AP1903, AP20187, dimeric FK506, or a dimeric FK506-like analog.

19. A polynucleotide comprising a nucleic acid sequence encoding the chimeric protein of any one of embodiments 10-18.

20. The polynucleotide of embodiment 19, wherein the polynucleotide comprises the nucleic acid sequence shown in SEQ ID NO: 8

21. An expression vector comprising the polynucleotide of embodiment 19 or 20.

22. An engineered immune cell comprising the chimeric protein of any one of embodiments 10-18 or the polynucleotide of embodiment 19 or 20.

23. The engineered immune cell of embodiment 22, wherein the cell further comprises a chimeric antigen receptor (CAR) or a polynucleotide encoding a CAR.

24. The engineered immune cell of embodiment 22 or 23, wherein the immune cell is a T cell.

25. A method of modulating an engineered immune cell in a subject, the method comprising administering a dimeric ligand to a subject that has previously been administered an engineered immune cell of any one of embodiments 22-24, wherein the dimeric ligand binds to the dimerization domain of the chimeric protein, and wherein caspase-9 activity is induced upon binding of the ligand to the dimerization domain.

26. The method of embodiment 25, wherein the ligand is AP1903.

27. A method of preparing an engineered immune cell, the method comprising introducing a polynucleotide of embodiment 6, 7, 19, or 20 or an expression vector of embodiment 8 or 21 into the immune cell.

The following examples are offered for illustrative purposes only, and are not intended to limit the scope of the disclosure in any way. Indeed, various modifications of the disclosure in addition to those shown and described herein will become apparent to those skilled in the art from the foregoing description and fall within the scope of the appended claims.

EXAMPLES

Example 1: Determination of Apoptosis-Inducing Activity of Chimeric Caspase 9 Proteins Containing Different Modified Caspase 9 Polypeptides This example determines the ability of various different chimeric caspase 9 proteins to induce apoptosis in T cells.

Each chimeric caspase 9 protein contains an FKBP12-dimerization domain and a modified caspase-9 polypeptide.

Example 1, Part A—Preparation of T Cells Containing Different Chimeric Caspase 9 Proteins Preparation of T Cells for Transduction Primary T cells were prepared from each of four different human blood donors ("Donor 1", "Donor 2", "Donor 3" and "Donor 8") as follows.

Peripheral blood mononuclear cells (PBMCs) were purified from whole blood from Stanford Blood cell Bank using SepMate-50 tubes (StemCell Technology, Cat No. 15450) and Ficoll-Paque Plus (GE, Cat No. 17-1440-03). Primary T cells were isolated with the Miltenyi Pan T Cell Isolation kit (Miltenyi, Cat #130-096-535) and frozen at −86 C until needed.

Preparation of Lentivirus Containing a Polynucleotide Encoding a Chimeric Caspase 9 Protein Containing a FKBP 12 Dimerization Domain and a Modified Caspase-9 Polypeptide Multiple different lentiviral vectors were generated. Each lentiviral vector contained a polynucleotide encoding a chimeric caspase 9 protein containing a FKBP12 dimerization domain and a modified caspase-9 polypeptide. The different lentiviral vectors encoded chimeric caspase-9 proteins having the same amino acid sequence, except for 1, 2, or 3 different amino acid mutations in the caspase-9 polypeptide. Lentiviral vectors containing polynucleotides encoding chimeric caspase 9 proteins having the following different modifications in the caspase-9 polypeptide were generated:

Single substitutions: R192K, E202K, C239N, G248L, E261S, N265E, S271A, S271Y, C272D, C272M, S274E, L275H, L275I, L275K, K280G, C287A, G288P, G289D, D330L, D330M, D330Q, S334V, P338W, F342H, I370E, D379E, D379V, S382I, L385W, V387A, A388W, A390N, Y397I, K398D, Q399I, P401I, N405Q, F406D, F406W, L407H, K409D, K409N;

Double substitutions: Q221R-V387A, Q221R-C287A, S242M-G289D, S271Y-D330M, D274E-D330M, S275E-D330M, D330L-I370E, D330L-D379E, D330M-F342H, D330M-I370E, D330M-D379E, D330M-V387A, D330M-A390N, D330M-K409N, G360D-L380V, V387A-K409N;

Triple substitution: D330M-D379E-K409N.

An exemplary amino acid sequence for a chimeric caspase-9 protein used with this experiment is provided below. This sequence is for a chimeric caspase 9 protein that contains the D330M-D379E double mutation in the caspase-9 polypeptide portion:

```
                                         (SEQ ID NO: 6)
GVQVETISPGDGRTFPKRGQTCVVHYTGMLEDGKK

VDSSRDRNKPFKFMLGKQEVIRGWEEGVAQMSVGQ

RAKLTISPDYAYGATGHPGIIPPHATLVFDVELLK

LESGGGSGVDGFGDVGALESLRGNADLAYILSMEP

CGHCLIINNVNFCRESGLRTRTGSNIDCEKLRRRF

SSLHFMVEVKGDLTAKKMVLALLELAQQDHGALDC

CVVVILSHGCQASHLQFPGAVYGTDGCPVSVEKIV
```

-continued
```
LFFIQACGGEQKDHGFEVASTSPEDESPGSNPEPD

NIFNGTSCPSLGGKPKATPFQEGLRTFDQLMAISS

LPTPSDIFVSYSTFPGFVSWRDPKSGSWYVETLDD

IFEQWAHSEELQSLLLRVANAVSVKGIYKQMPGCF

NFLRKKLFFKTS
```

In the above chimeric protein, the following components are notated (in order from the N-terminus to the C-terminus):

Underlined portion: FKBP12 dimerization domain, with the F36V mutation. The amino acid sequence of the FKBP12 dimerization domain is also separately provided here: GVQVETISPGDGRTFPKRGQTCVVHYTGMLEDGKK VDSSRDRNKPFKFMLGKQEV IRGWEEGVAQMSVGQRAKLTISPDYAYGATGHPGIIP-PHATLVFDVELLKLES (SEQ ID NO: 4) In the immediately preceding sequence, the V from the F36V mutation is underlined.

Italicized portion: a linker region. The amino acid sequence of the linker is also separately provided here: GGGSGVD (SEQ ID NO: 5).

Bold portion: modified caspase 9 polypeptide. The amino acid sequence of the modified caspase 9 polypeptide is also separately provided here: GFGDVGALESLRGNADLAY-ILSMEPCGHCLIINNVNFCRESGLRTRTGSNIDCEKLR RRFSSLHFMVEVKGDLTAKKMVLALLE-LAQQDHGALDCCVVVILSHGCQASHLQF PGAVYGTDGCPVS-VEKIVNIFNGTSCPSLGGKPKLFFIQACGGEQKDHG FEVASTSP EDESPGSNPEPDATPFQEGLRTFDQL-MAISSLPTPSDIFVSYSTFPGFVSWRDPKSGS WYVETLDDIFEQWAHSEELQSLLLRVA-NAVSVKGIYKQMPGCFNFLRKKLFFKTS (SEQ ID NO: 3) In the immediately preceding sequence, the M from the D330M mutation and the E from the D379E mutation are underlined. The modified caspase 9 polypeptide of SEQ ID NO: 3 does not contain the CARD domain of the full length wild-type caspase 9 protein.

Other chimeric caspase-9 proteins used with this Example have the same structure as the chimeric caspase-9 protein as show in in SEQ ID NO: 6, except for the having the respective amino acid substitution(s) as indicated for each protein.

Exemplary nucleic acid sequences encoding the above chimeric caspase 9 protein (i.e. containing the D330M-D379E double mutation) and portions thereof are in Table 2.

TABLE 2

| SEQ ID NO: | Sequence | Description |
|---|---|---|
| 8 | GGAGTGCAGGTCGAAACAATCTCAC CCGGCGATGGACGGACATTCCCCAA AAGAGGACAGACTTGCGTCGTGCAT TATACCGGCATGCTGGAGGACGGCA AGAAGGTGGACAGCTCCCGCGATCG GAACAAGCCCTTCAAGTTTATGCTG GGCAAGCAGGAAGTGATCAGGGGAT GGGAGGAGGGAGTGGCACAGATGAG CGTGGGACAGAGGGCAAAGCTGACC ATCTCCCCAGACTACGCATATGGAG CAACAGGACACCCTGGAATCATCCC ACCTCACGCCACACTGGTGTTCGAT | Nucleic acid sequence encoding the amino acid sequence of SEQ ID NO: 6 (chimeric caspase 9 protein that contains the D330M- D379E |

TABLE 2-continued

| SEQ ID NO: | Sequence | Description |
|---|---|---|
| | GTGGAGCTGCTGAAGCTGGAGTCCG GAGGAGGATCTGGAGTGGACGGATT TGGCGATGTGGGCGCCCTGGAGTCT CTGAGAGGCAATGCCGATCTGGCCT ACATCCTGAGCATGGAGCCTTGCGG CCACTGTCTGATCATCAACAATGTG AACTTCTGCAGGGAGTCCGGCCTGA GAACCAGGACAGGCTCTAATATCGA CTGTGAGAAGCTGCGGAGAAGGTTC TCTAGCCTGCACTTTATGGTGGAGG TGAAGGGCGATCTGACCGCCAAGAA GATGGTGCTGGCCCTGCTGGAGCTG GCCCAGCAGGACCACGGCGCCCTGG ATTGCTGCGTGGTGGTCATCCTGTC TCACGGATGCCAGGCCAGCCACCTG CAGTTCCCAGGAGCCGTGTATGGAA CCGACGGATGTCCCGTGAGCGTGGA GAAGATCGTGAACATCTTTAATGGC ACAAGCTGCCCATCCCTGGGAGGCA AGCCAAAGCTGTTCTTTATCCAGGC CTGTGGCGGCGAGCAGAAGGATCAC GGCTTTGAGGTGGCCAGCACCTCCC CAGAGGACGAGTCTCCTGGCAGCAA CCCAGAGCCCGATGCCACCCCTTTC CAGGAGGGCCTGCGCACATTTGACC AGCTGATGGCCATCTCCTCTCTGCC TACCCCATCCGACATCTTCGTGTCT TACAGCACATTCCCTGGCTTCGTGA GCTGGCGGGACCCCAAGTCCGGCTC TTGGTACGTGGAGACACTGGACGAT ATCTTTGAGCAGTGGGCACACAGCG AGGAGCTGCAGTCCCTGCTGCTGAG AGTGGCCAACGCCGTGTCCGTGAAG GGCATCTACAAGCAGATGCCAGGCT GCTTCAATTTTCTGAGGAAAAAACT GTTCTTCAAAACTAGC | double mutation) |
| 9 | GGAGTGCAGGTCGAAACAATCTCAC CCGGCGATGGACGGACATTCCCCAA AAGAGGACAGACTTGCGTCGTGCAT TATACCGGCATGCTGGAGGACGGCA AGAAGGTGGACAGCTCCCGCGATCG GAACAAGCCCTTCAAGTTTATGCTG GGCAAGCAGGAAGTGATCAGGGGAT GGGAGGAGGGAGTGGCACAGATGAG CGTGGGACAGAGGGCAAAGCTGACC ATCTCCCCAGACTACGCATATGGAG CAACAGGACACCCTGGAATCATCCC ACCTCACGCCACACTGGTGTTCGAT GTGGAGCTGCTGAAGCTGGAGTCC | Nucleic acid sequence encoding the amino acid sequence of SEQ ID NO: 4 (FKBP12 dimerization domain, containing the F36V mutation) |
| 10 | GGAGGAGGATCTGGAGTGGAC | Nucleic acid sequence encoding the amino acid sequence of SEQ ID NO: 5 (linker region) |
| 11 | GGATTTGGCGATGTGGGCGCCCTGG AGTCTCTGAGAGGCAATGCCGATCT GGCCTACATCCTGAGCATGGAGCCT TGCGGCCACTGTCTGATCATCAACA ATGTGAACTTCTGCAGGGAGTCCGG CCTGAGAACCAGGACAGGCTCTAAT ATCGACTGTGAGAAGCTGCGGAGAA GGTTCTCTAGCCTGCACTTTATGGT GGAGGTGAAGGGCGATCTGACCGCC AAGAAGATGGTGCTGGCCCTGCTGG AGCTGGCCCAGCAGGACCACGGCGC CCTGGATTGCTGCGTGGTGGTCATC CTGTCTCACGGATGCCAGGCCAGCC ACCTGCAGTTCCCAGGAGCCGTGTA TGGAACCGACGGATGTCCCGTGAGC GTGGAGAAGATCGTGAACATCTTTA | Nucleic acid sequence encoding the amino acid sequence of SEQ ID NO: 3 (modified caspase 9 polypeptide, containing D330M and D379E mutations). Codons encoding the M from the |

TABLE 2-continued

| SEQ ID NO: | Sequence | Description |
|---|---|---|
| | ATGGCACAAGCTGCCCATCCCTGGG AGGCAAGCCAAAGCTGTTCTTTATC CAGGCCTGTGGCGGCGAGCAGAAGG ATCACGGCTTTGAGGTGGCCAGCAC CTCCCCAGAGGACGAGTCTCCTGGC AGCAACCCAGAGCCCGATGCCACCC CTTTCCAGGAGGGCCTGCGCACATT TGACCAGCTGATGGCCATCTCCTCT CTGCCTACCCCATCCGACATCTTCG TGTCTTACAGCACATTCCCTGGCTT CGTGAGCTGGCGGGACCCCAAGTCC GGCTCTTGGTACGTGGAGACACTGG ACGATATCTTTGAGCAGTGGGCACA CAGCGAGGAGCTGCAGTCCCTGCTG CTGAGAGTGGCCAACGCCGTGTCCG TGAAGGGCATCTACAAGCAGATGCC AGGCTGCTTCAATTTTCTGAGGAAA AAACTGTTCTTCAAAACTAGC | D330M mutation and the E from the D379E mutation are underlined. |

Each different lentiviral vector was generated as follows. HEK293T cells were transfected with 3 lentiviral plasmids containing the genome plasmid pLVX-EF1a-GFP-P2A-FKBP-F36V-Casp9, the gag/pol plasmid psPAX2 and the envelope plasmid pMD.2G (GenScript). The genome plasmid contains the polynucleotide that encodes the chimeric caspase 9 protein with the respective caspase 9 substitution(s) of interest. The genome plasmid also encodes green fluorescent protein (GFP), to facilitate the identification of cells transfected with the polynucleotide that encodes the chimeric caspase 9 protein. The generated respective lentiviral vectors were released into the supernatant of each different HEK293T cell transfection culture.

Lentivirus-Mediated Transduction of T Cells with a Polynucleotide Encoding Chimeric Caspase 9 Protein Constructs to Generate T Cells Containing Chimeric Caspase 9 Proteins T cells which contained a chimeric caspase 9 protein were generated as follows.

Previously-frozen primary T cells were thawed and activated with ImmunoCult Human CD3/CD28 T cell activator (StemCell, Cat #10971). 48 hours later, a lentiviral vector which contains a polynucleotide encoding a chimeric caspase 9 protein as described above was added to the activated primary T cells for transduction. Different lentiviral vectors were added to different samples of the primary T cells to test the activity of the different chimeric caspase 9 proteins. The respective lentiviral vectors were provided to the T cells in filtered supernatant from the HEK293T cells. T cells transduced with a polynucleotide encoding a chimeric caspase 9 protein subsequently expressed the respective chimeric caspase 9 protein.

As shown in Tables 3-7 below, T cells from each of Donors 1, 2, and 3 were transfected with polynucleotides encoding multiple different chimeric caspase 9 proteins.

Also, for comparison purposes, attempts were made to prepare a chimeric caspase-9 protein containing a wild-type caspase-9 polypeptide. However, these efforts were not successful, as HEK293T cells transfected with plasmids containing wild-type caspase-9 polypeptide constructs did not survive and yield lentivirus for transfecting T cells. Without being bound by theory, it is believed that this is due to the relatively high basal activity of the wild-type caspase-9 polypeptide (which can be expressed in HEK293T cells upon introduction of the plasmids into the cells), and that this also indicates that all of the caspase-9 mutants listed in Tables 3-7 below have less basal activity than wild-type caspase-9.

Example 1, Part B—Assaying the Induction of Apoptosis in T Cells Containing Different Chimeric Caspase 9 Proteins T cells containing different chimeric caspase 9 proteins prepared as described in part A above were assayed for apoptosis in response to the dimeric ligand AP1903.

For each assay, about 1,000,000 cells containing a particular chimeric caspase 9 protein were incubated with or without 10 nM AP1903 for 3 or 4 days. On the $3^{rd}$ or $4^{th}$ day, the cells were measured by flow cytometry to determine the percentage of live cells that are GFP positive (+). (GFP is a marker for the chimeric caspase 9 protein.) Thus, it can be extrapolated that the greater the % of live GFP+ cells, the lower the apoptotic activity of the respective chimeric caspase 9 protein in this assay.

The different combinations of donor cells and chimeric caspase 9 proteins assayed are listed in Tables 3-7 below, with the results of the assays.

Figure 2:
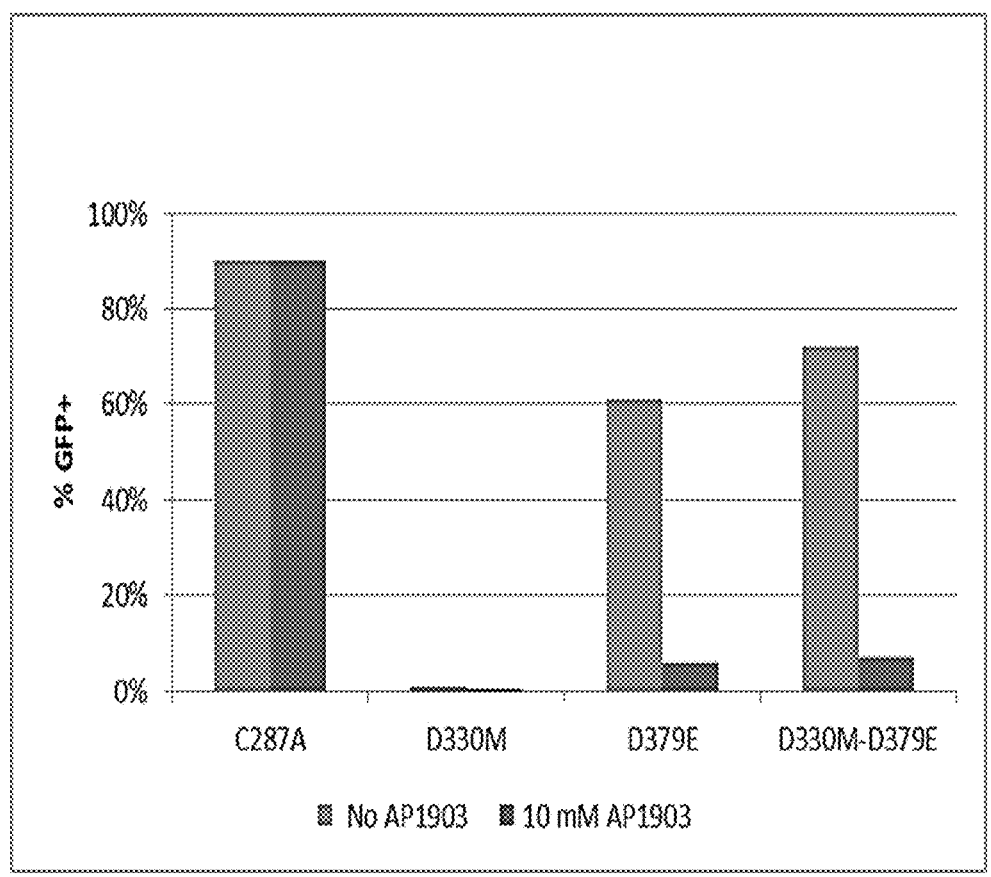
FIG. 2 is a bar graph indicating the induction of apoptosis by different chimeric caspase-9 proteins in response to AP1903, in host cells from Donor #1.
Figure 3:
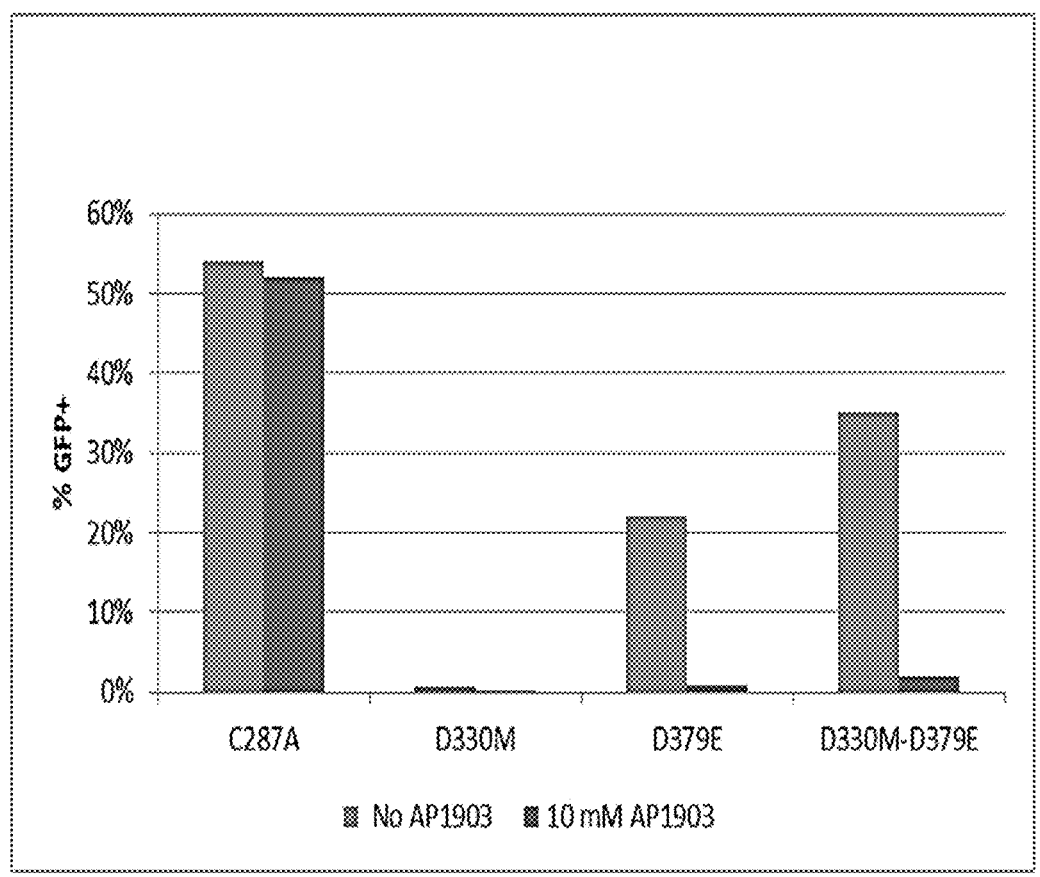
FIG. 3 is a bar graph indicating the induction of apoptosis by different chimeric caspase-9 proteins in response to AP1903, in host cells from Donor #2.

The results listed in Tables 3 and 4 below are also presented in graph form in FIG. 1 and FIG. 2, respectively. In FIG. 1 and FIG. 2, the different chimeric caspase-9 proteins are listed on the X-axis, and the % GFP positive cells is listed on the Y-axis. Also, for each different chimeric caspase-9 protein, there are two adjacent bars. The left-side bar is for the cells incubated without AP1903, and the right-side bar is for the corresponding cells incubated with AP1903.

TABLE 3

Donor # 1, primary T cells, % GFP positive cells, 4 days after AP1903

| Caspase 9 substitution | % GFP, 0 mM AP1903 | % GFP, 10 mM AP1903 |
| --- | --- | --- |
| C287A | 90% | 90% |
| D330M | 0.80% | 0.03% |
| D379E | 61% | 6% |
| D330M-D379E | 72% | 7% |

TABLE 4

Donor # 2, primary T cells, % GFP positive cells, 4 days after AP1903

| Caspase 9 substitution | % GFP, 0 mM AP1903 | % GFP, 10 mM AP1903 |
| --- | --- | --- |
| C287A | 54% | 52% |
| D330M | 0.60% | 0.20% |
| D379E | 22% | 1% |
| D330M-D379E | 35% | 2% |

TABLE 5

Donor # 1, primary T cells, % GFP positive cells, 4 days after AP1903

| Caspase 9 substitution | % GFP, 0 mM AP1903 | % GFP, 10 mM AP1903 |
| --- | --- | --- |
| C287A | 90.4 | 90.2 |
| D330M | 0.83 | 0.034 |
| D379E | 60.6 | 6.43 |
| V387A | 47.7 | 4.16 |
| K409N | 77 | 26.8 |
| D330M-D379E | 72.3 | 6.95 |
| V387A-K409N | 89.1 | 89.3 |
| D330M-K409N | 83.4 | 35.5 |
| D330M-D379E-K409N | 89.4 | 90.3 |
| D379E-N405Q | 89.1 | 87.9 |
| Untransduced | 0.035 | 0 |

TABLE 6

Donor # 1, primary T cells, % GFP positive cells, 4 days after AP1903

| Caspase 9 substitution | % GFP, 0 mM AP1903 | % GFP, 10 mM AP1903 |
| --- | --- | --- |
| C287A Q221R | 74.6 | 76.9 |
| R192K | 2.7 | 0.13 |
| E202K | 3.18 | 0.21 |
| C239N | 1.56 | 0.13 |
| G248L | 29.6 | 30.7 |
| E261S | 20.6 | 20.6 |
| N265E | 2.75 | 0.23 |
| S271A | 2.15 | 0.19 |
| S271Y | 5.55 | 0.54 |
| C272D | 25 | 26.4 |
| C272M | 28.9 | 25.7 |
| S274E | 9.91 | 1.6 |
| L275H | 19.4 | 22 |
| L275I | 18 | 10.1 |
| L275K | 16.9 | 17.7 |
| K280G | 24.8 | 25.7 |
| G288P | 32 | 33.1 |
| G289D | 33.4 | 34.1 |
| D330L | 6.61 | 0.37 |
| D330Q | 4.06 | 0.19 |
| S334V | 1.53 | 0.11 |
| P338W | 6.56 | 2.12 |
| C287A | 74.6 | 76 |
| F342H | 6.95 | 0.5 |
| I370E | 21.3 | 1.8 |
| D379V | 18.1 | 18.1 |
| S382I | 28.3 | 24.6 |
| L385W | 8.01 | 9.89 |
| A388W | 30.7 | 33 |
| A390N | 10.6 | 0.5 |
| Y397I | 19.4 | 15.6 |
| K398D | 27.9 | 27.5 |
| Q399I | 25.5 | 25.6 |
| P401I | 23.8 | 24.2 |
| F406D | 22.4 | 22.7 |
| F406W | 7.71 | 0.64 |
| L407H | 26.5 | 22 |
| K409D | 30.3 | 30.7 |
| S242M-G289D | 27.4 | 27.5 |
| G360D-L380V | 25.7 | 27.4 |
| D330M-D379E | 53.4 | 5.04 |
| Q221R-V387A | 16.1 | 3.85 |
| Untransduced | 0.08 | 0.17 |

TABLE 7

Donor # 3, primary T cells, % GFP positive cells,
4 days after AP1903

| Caspase 9 substitution | % GFP, 0 mM AP1903 | % GFP, 10 mM AP1903 |
|---|---|---|
| C287A | 87 | 86 |
| D330M-D379E | 71 | 7 |
| S271Y | 7 | 0.5 |
| S271Y-D330M | 18 | 1 |
| S274E | 20 | 3 |
| S274E-D330M | 36 | 2 |
| D330L | 10 | 0.4 |
| F342H | 7 | 0.3 |
| D330M-F342H | 23 | 1 |
| I370E | 37 | 2 |
| D330L-I370E | 51 | 8 |
| D330M-I370E | 47 | 4 |
| D330L-D379E | 48 | 5 |
| Q221R-V387A | 19 | 2 |
| D330M-V387A | 60 | 9 |
| A390N | 14 | 0.5 |
| D330M-A390N | 24 | 1 |
| NTD | 0.1 | 0.1 |

As indicated in the tables above, multiple different modified caspase-9 polypeptides provided herein have apoptotic activity that is induced by AP1903. This can be seen, for example, by comparing the difference in the % GFP positive cells in 0 mM AP1903 as compared to in 10 mM AP1903 for each different modified caspase-9. Also, typically, it is generally desirable to have a high % GFP+ cells in the absence of AP1903 (indicating low basal activity for the chimeric caspase 9 protein), and a large difference in the % of GFP+ cells between the cells incubated in 10 mM AP1903 vs the cells incubated in 0 mM AP1903. A large difference in the % GFP+ cells between these two populations indicates that the activity of the chimeric caspase 9 protein can be induced; if the difference isn't large between the two populations, it indicates that either i) the chimeric caspase 9 protein has a relatively high basal caspase 9 activity (in the case of low % GFP+ in the absence of ligand) or ii) it has a relatively low caspase 9 activity, even in the presence of AP1903 (in the case of high % GFP+ in the presence of ligand). For example, some of the chimeric caspase 9 proteins as shown above that have attractive activity profiles include, for example: single mutations: S271Y, S274E, D330L, D330M, F342H, I370E, D379E, V387A, A390N, F406W, and K409N; double mutations: Q221R-V387A, D330L-I370E, D330L-D379E, D330M-S271Y, D330M-S274E, D330M-F342H, D330M-I370E, D330M-D379E, D330M-V387A, D330M-A390N, and D330M-K409N.

Example 2—Assaying the Expression Level and the Induction of Apoptosis in T Cells Comprising Different Chimeric Caspase-9 Proteins and a CAR T cells derived from donor #8 comprising various different chimeric caspase 9 proteins, some of which further comprise a CAR were prepared as described in part 1A above and were assayed for expression of chimeric caspase-9 and for induced apoptosis in response to the dimeric ligand AP1903.

For each assay, about 1,000,000 cells containing a particular chimeric caspase 9 protein were incubated with or without 10 nM AP1903 for 3 or 4 days. On days 1, 2 and 3 post-AP1903 (FIGS. 6, 7, and 8, respectively), the cells were measured by flow cytometry to determine the percentage of live cells that are GFP positive (+) (GFP is a marker for the chimeric caspase 9 protein). Thus, it can be extrapolated that the greater the % of live GFP+ cells, the lower the apoptotic activity of the respective chimeric caspase 9 protein in this assay.

Figure 4:
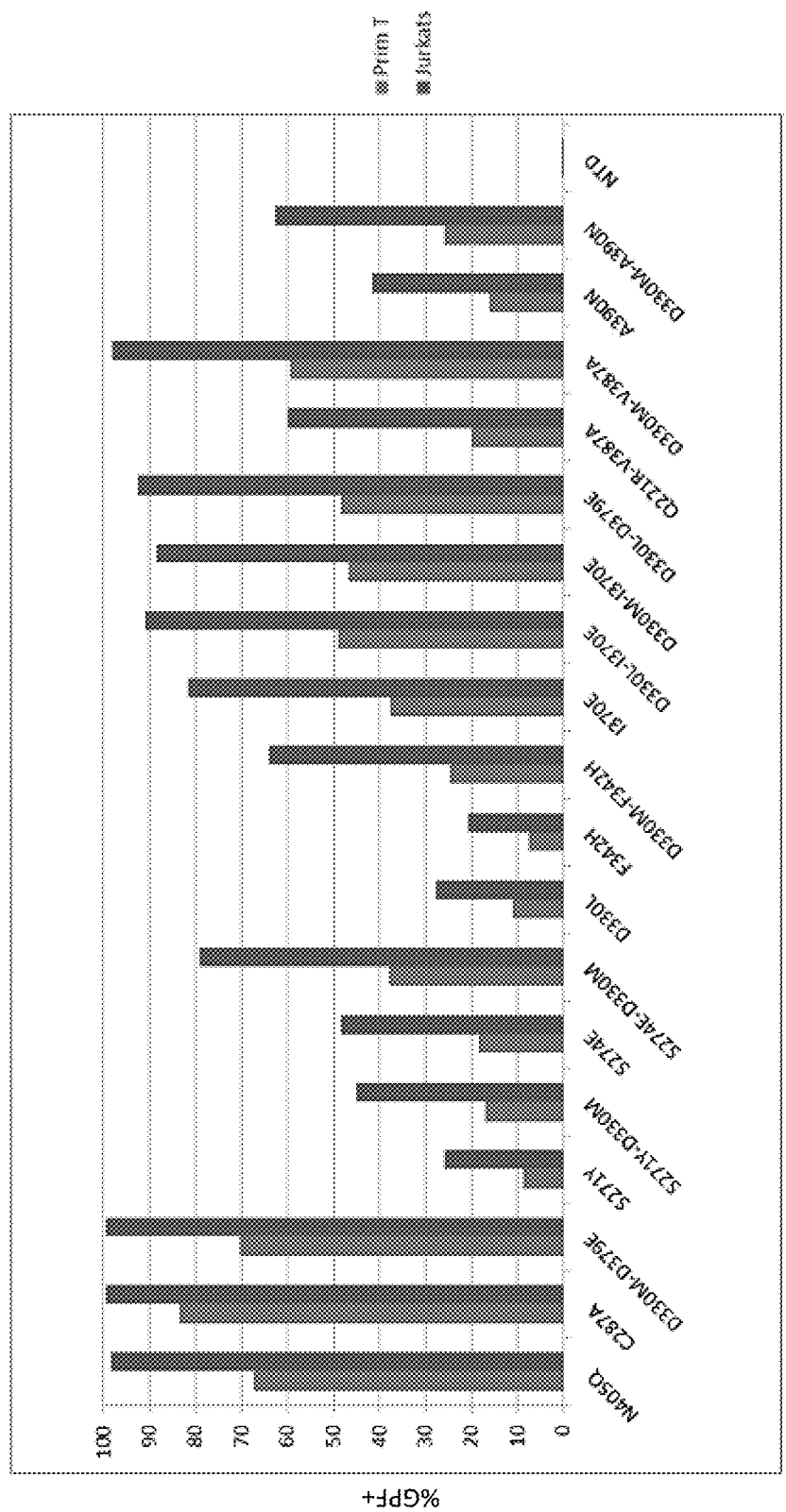
FIG. 4 is a bar graph indicating the expression level of different chimeric caspase-9 proteins comprising one or more mutations four days after transduction of primary T cells (lefthand bar of the pair) or Jurkat cells (righthand bar of the pair).

The results are presented in FIGS. 4-9. In FIGS. 4-9, the different chimeric caspase-9 proteins are listed on the X-axis, and the % GFP positive or % CAR positive cells is listed on the Y-axis. In FIG. 4, for each different chimeric caspase-9 protein, there are two adjacent bars. The left-side bar represents expression in primary T cells and the right-side bar represents expression in Jurkat cells.

Figure 5:
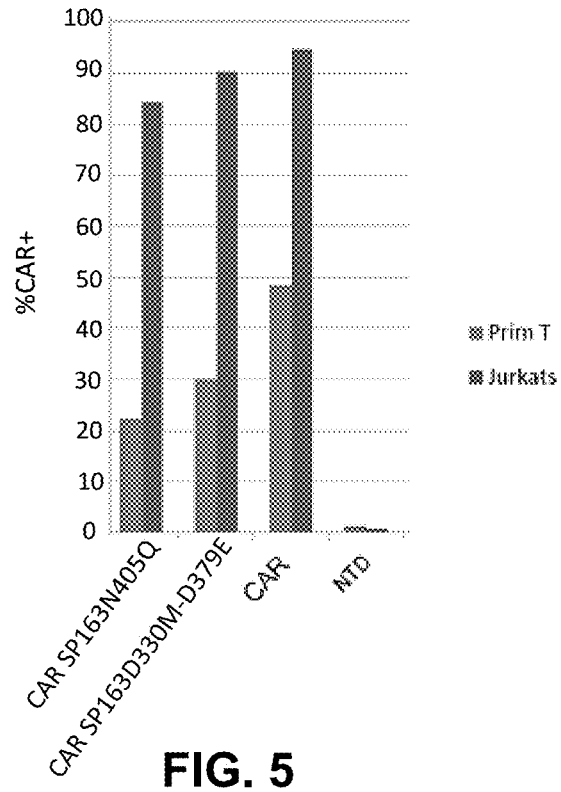
FIG. 5 is a bar graph indicating expression levels of CAR positive primary T cells (lefthand bar of the pair) or Jurkat cells (righthand bar of the pair).

In FIG. 5 the bar graph indicating expression levels of CAR positive primary T cells (lefthand bar of the pair) or Jurkat cells (righthand bar of the pair).

Figure 6:
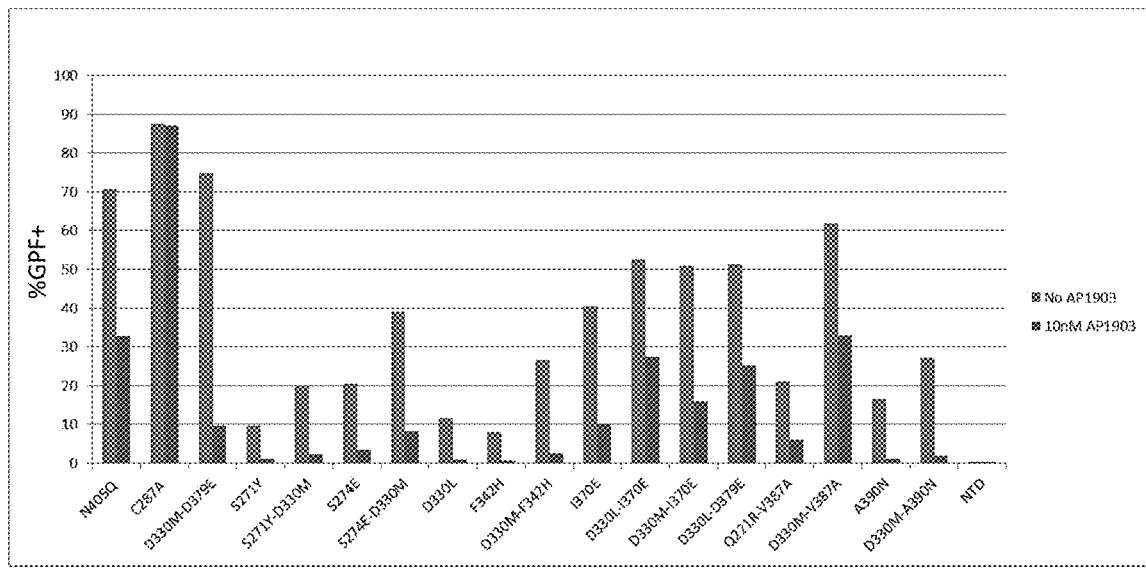
FIG. 6 is a bar graph indicating the apoptosis activity of different chimeric caspase-9 proteins comprising one or more mutations expressed on primary T cells from Donor #8 in the presence or absence of AP1903, 1 day post-AP1903.
Figure 7:
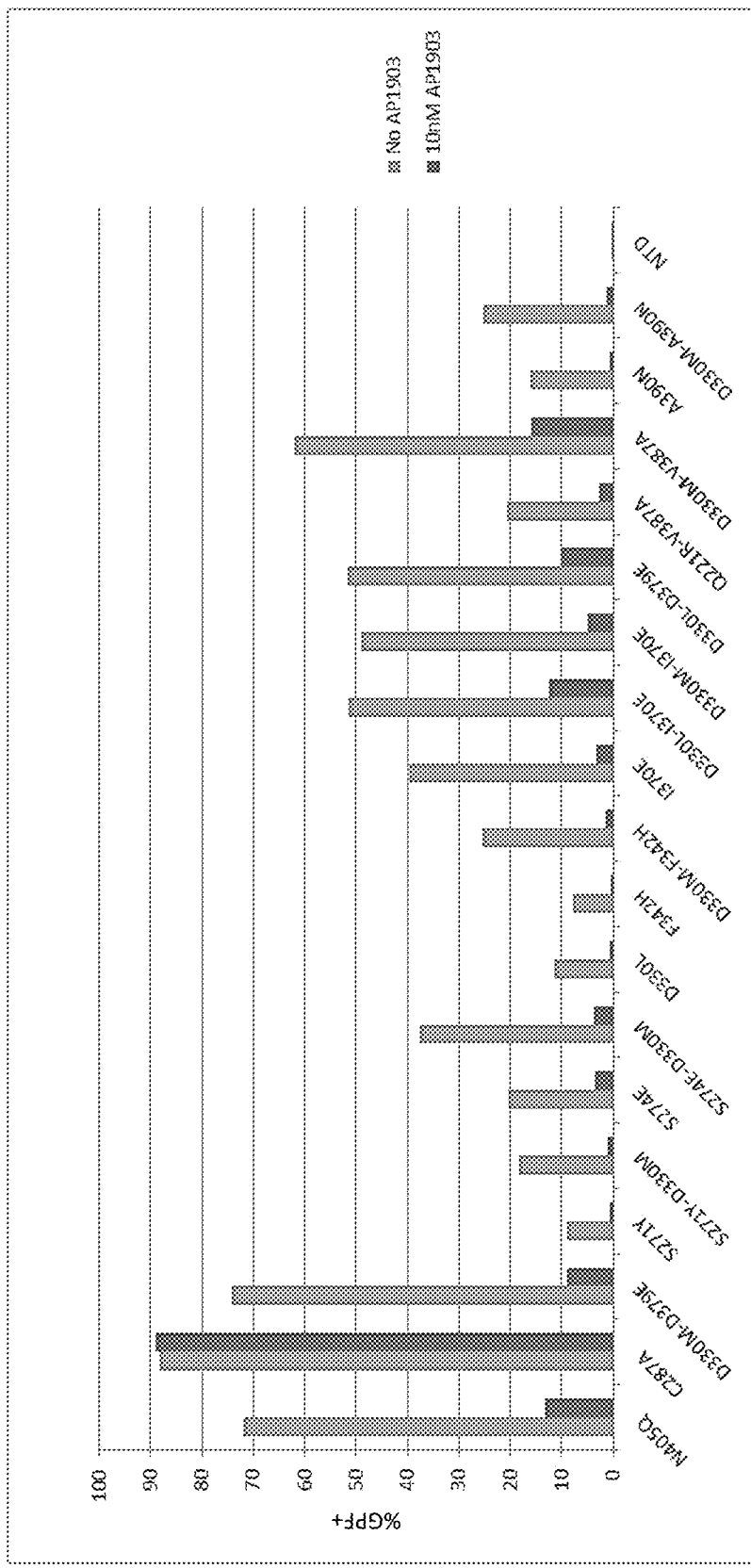
FIG. 7 is a bar graph indicating the apoptosis activity of different chimeric caspase-9 proteins comprising one or more mutations expressed on primary T cells from Donor #8, in the presence or absence of AP1903, 2 days post-AP1903.
Figure 8:
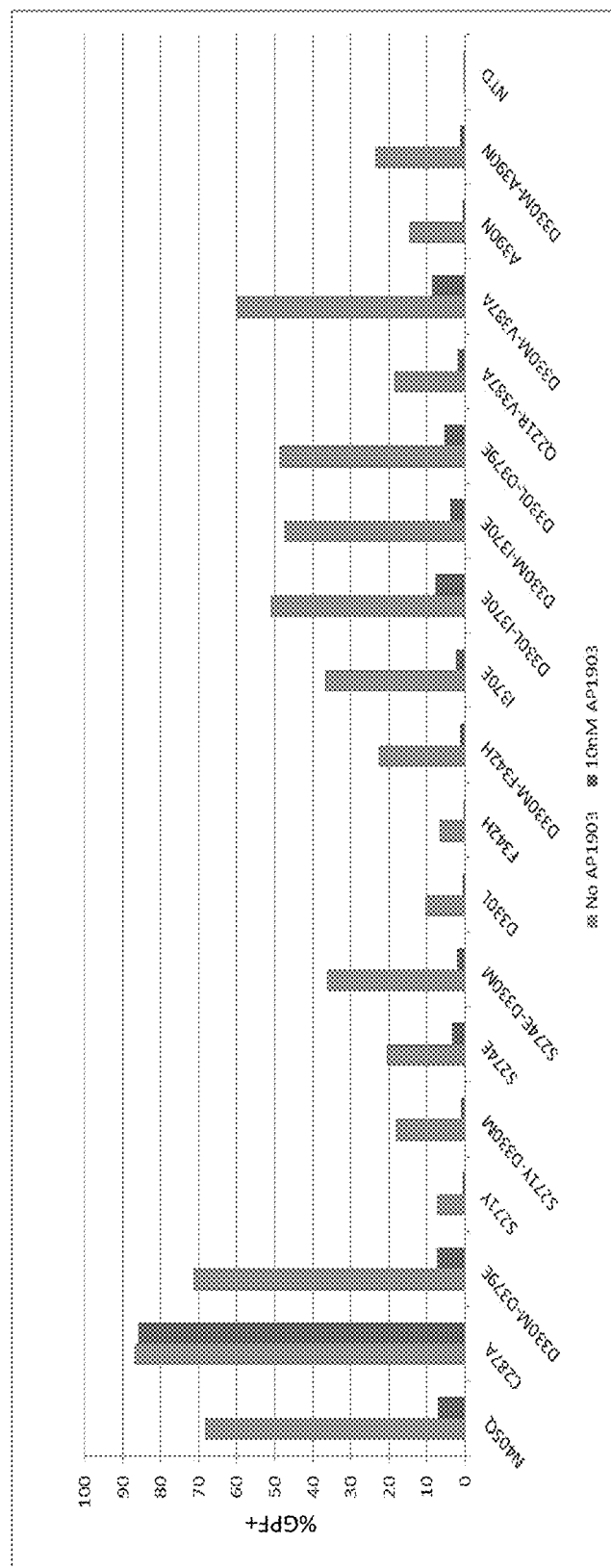
FIG. 8 is a bar graph indicating the apoptosis activity of different chimeric caspase-9 proteins comprising one or more mutations expressed on primary T cells from Donor #8 in the presence or absence of AP1903, 3 days post-AP1903.
Figure 9:
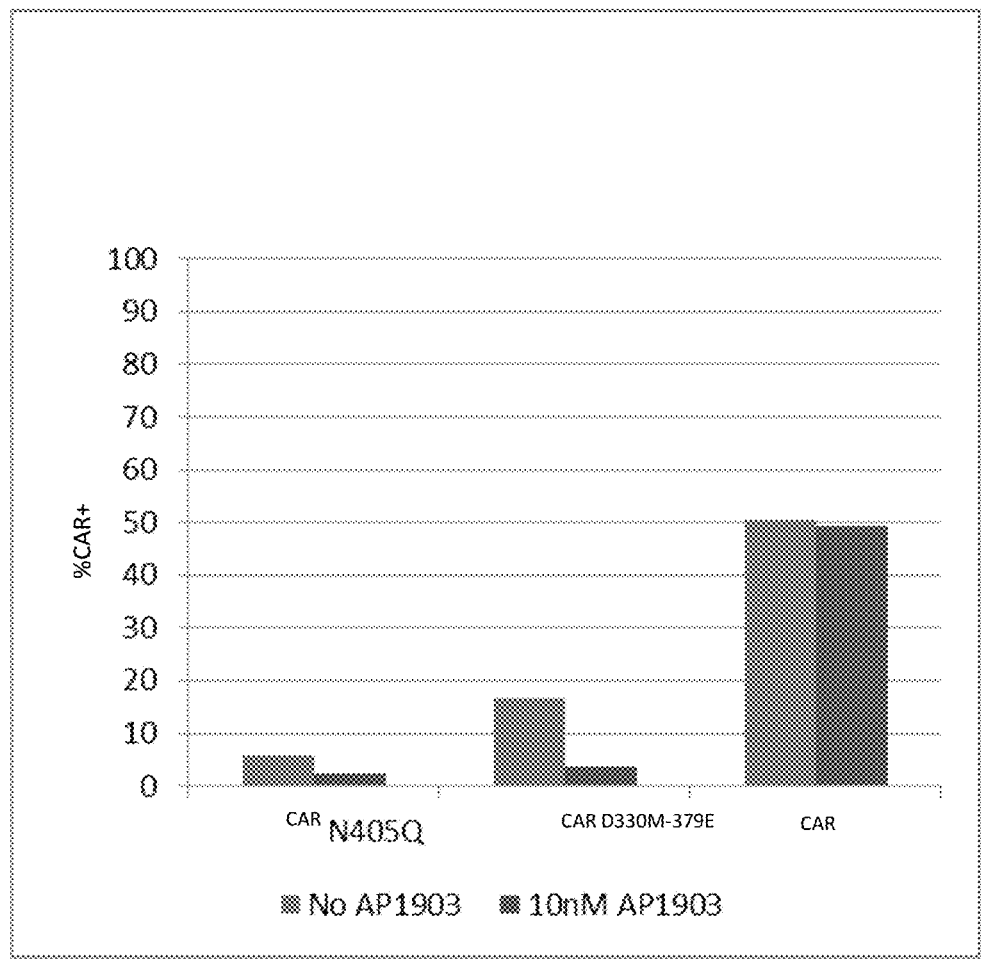
FIG. 9 is a bar graph indicating the apoptosis activity of different chimeric caspase-9 proteins comprising one or more mutations in combination with a CAR expressed on primary T cells from Donor #8 in the presence or absence of AP1903, 4 days post AP 1903.

In FIGS. 6-9, for each different chimeric caspase-9 protein, expressed with or without a CAR, there are two adjacent bars. The left-side bar is for the cells incubated without AP1903, and the right-side bar is for the corresponding cells incubated with AP1903. FIG. 6 shows that apoptosis induced by the D330M-D379E construct is approximately 3-fold faster on Day 1 than apoptosis induced by the N405Q construct. This observation is consistent with the application of the D330M-D379E construct as a fast-acting "safety switch" for CAR-T therapies.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

The invention claimed is:

1. A polynucleotide comprising a nucleic acid sequence encoding a modified caspase-9 polypeptide comprising an amino acid sequence having at least 90% sequence identity to SEQ ID NO: 2, and at least one amino acid substitution, wherein the at least one amino acid substitution is at an amino acid position selected from the group consisting of S271, S274, F342, I370, D379, V387, A390, and K409, wherein each amino acid position refers to the position of the respective amino acid in SEQ ID NO: 1.

2. The polynucleotide of claim 1, wherein the polynucleotide comprises the nucleic acid sequence of SEQ ID NO: 11.

3. An expression vector comprising the polynucleotide of claim 1.

4. An engineered immune cell comprising the polynucleotide of claim 1.

5. A polynucleotide comprising a nucleic acid sequence encoding a modified caspase-9 polypeptide comprising an amino acid sequence having at least 95% to 99% sequence identity to SEQ ID NO: 2, and at least one amino acid substitution, wherein the at least one amino acid substitution is selected from the group consisting of S271Y, S274E, F342H, I370E, D379E, V387A, A390N, and K409N, wherein each amino acid position refers to the position of the respective amino acid in SEQ ID NO: 1.

6. The polynucleotide of claim 1, wherein the modified caspase-9 polypeptide comprises an amino acid sequence having at least 95% to 99% sequence identity to SEQ ID NO: 2, and at least two amino acid substitutions, wherein the at least two amino acid substitutions are at the amino acid positions selected from the group consisting of Q221-V387, D330-I370, D330-D379, D330-S271, D330-S274, D330-F342, D330-D379, D330-V387, D330-A390, and D330-K409, and wherein each amino acid position refers to the position of the respective amino acid in SEQ ID NO: 1.

7. The polynucleotide of claim 6, wherein the polypeptide comprises at least two amino acid substitutions selected from the group consisting of Q221R-V387A, D330L-I370E, D330L-D379E, D330M-S271Y, D330M-S274E, D330M-F342H, D330M-I370E, D330M-D379E, D330M-V387A, D330M-A390N, and D330M-K409N.

8. The polynucleotide of claim 7, wherein the polypeptide comprises the amino acid sequence of SEQ ID NO: 3.

9. The polynucleotide of claim 1, wherein the at least one amino acid substitution is at an amino acid position selected from the group consisting of S271, D379, V387, A390, and K409.

10. The polynucleotide of claim 1, wherein the at least one amino acid substitution is at an amino acid position selected from the group consisting of D379 and V387.

11. The polynucleotide of claim 5, wherein the at least one amino acid substitution is selected from the group consisting of S271Y, D379E, V387A, A390N, and K409N.

12. The polynucleotide of claim 5, wherein the at least one amino acid substitution is D379E.

13. The polynucleotide of claim 5, wherein the at least one amino acid substitution is selected from the group consisting of V387A.

14. The polynucleotide of claim 5, wherein the at least one amino acid substitution is A390N.

15. The polynucleotide of claim 5, wherein the at least one amino acid substitution is K409N.

16. The polynucleotide of claim 5, wherein the at least one amino acid substitution is selected from the group consisting of D379E and V387A.

17. The polynucleotide of claim 6, wherein the at least two amino acid substitutions are at the amino acid positions D330-D379 or D330-V387.

18. The polynucleotide of claim 17, wherein the polypeptide comprises at least two amino acid substitutions of D330M-D379E or D330M-V387A.

19. The polynucleotide of claim 17, wherein the polypeptide comprises at least two amino acid substitutions of D330M-D379E.

20. The polynucleotide of claim 17, wherein the polypeptide comprises at least two amino acid substitutions of D330M-V387A.

21. An expression vector comprising the polynucleotide of claim 5.

22. An engineered immune cell comprising the polynucleotide of claim 5.

23. An expression vector comprising the polynucleotide of claim 6.

24. An engineered immune cell comprising the polynucleotide of claim 6.

25. The polynucleotide of claim 1, wherein the polynucleotide comprises a nucleic acid sequence encoding a modified caspase-9 polypeptide comprising an amino acid sequence having at least 95% sequence identity to SEQ ID NO: 2.

26. The polynucleotide of claim 1, wherein the polynucleotide comprises a nucleic acid sequence encoding a modified caspase-9 polypeptide comprising an amino acid sequence having at least 97% sequence identity to SEQ ID NO: 2.

27. The polynucleotide of claim 1, wherein the polynucleotide comprises a nucleic acid sequence encoding a modified caspase-9 polypeptide comprising an amino acid sequence having at least 98% sequence identity to SEQ ID NO: 2.

28. The polynucleotide of claim 1, wherein the polynucleotide comprises a nucleic acid sequence encoding a modified caspase-9 polypeptide comprising an amino acid sequence having at least 99% sequence identity to SEQ ID NO: 2.

29. An engineered immune cell comprising the polynucleotide of claim 25.

30. An engineered immune cell comprising the polynucleotide of claim 26.

31. An engineered immune cell comprising the polynucleotide of claim 27.

32. An engineered immune cell comprising the polynucleotide of claim 28.

33. A method of preparing an engineered immune cell, the method comprising introducing the polynucleotide of claim 1 into the immune cell.

34. A method of preparing an engineered immune cell, the method comprising introducing the polynucleotide of claim 5 into the immune cell.

35. A method of preparing an engineered immune cell, the method comprising introducing the polynucleotide of claim 6 into the immune cell.

* * * * *

SEQUENCE LISTING

<160> NUMBER OF SEQ ID NOS: 33

<210> SEQ ID NO 1
<211> LENGTH: 416

<212> TYPE: PRT
<213> ORGANISM: Homo sapiens

<400> SEQUENCE: 1

Met Asp Glu Ala Asp Arg Arg Leu Leu Arg Cys Arg Leu Arg Leu
1               5                   10                  15

Val Glu Glu Leu Gln Val Asp Gln Leu Trp Asp Ala Leu Leu Ser Arg
            20                  25                  30

Glu Leu Phe Arg Pro His Met Ile Glu Asp Ile Gln Arg Ala Gly Ser
        35                  40                  45

Gly Ser Arg Arg Asp Gln Ala Arg Gln Leu Ile Ile Asp Leu Glu Thr
    50                  55                  60

Arg Gly Ser Gln Ala Leu Pro Leu Phe Ile Ser Cys Leu Glu Asp Thr
65                  70                  75                  80

Gly Gln Asp Met Leu Ala Ser Phe Leu Arg Thr Asn Arg Gln Ala Ala
                85                  90                  95

Lys Leu Ser Lys Pro Thr Leu Glu Asn Leu Thr Pro Val Val Leu Arg
            100                 105                 110

Pro Glu Ile Arg Lys Pro Glu Val Leu Arg Pro Glu Thr Pro Arg Pro
        115                 120                 125

Val Asp Ile Gly Ser Gly Gly Phe Gly Asp Val Gly Ala Leu Glu Ser
    130                 135                 140

Leu Arg Gly Asn Ala Asp Leu Ala Tyr Ile Leu Ser Met Glu Pro Cys
145                 150                 155                 160

Gly His Cys Leu Ile Ile Asn Asn Val Asn Phe Cys Arg Glu Ser Gly
                165                 170                 175

Leu Arg Thr Arg Thr Gly Ser Asn Ile Asp Cys Glu Lys Leu Arg Arg
            180                 185                 190

Arg Phe Ser Ser Leu His Phe Met Val Glu Val Lys Gly Asp Leu Thr
        195                 200                 205

Ala Lys Lys Met Val Leu Ala Leu Leu Glu Leu Ala Gln Gln Asp His
    210                 215                 220

Gly Ala Leu Asp Cys Cys Val Val Val Ile Leu Ser His Gly Cys Gln
225                 230                 235                 240

Ala Ser His Leu Gln Phe Pro Gly Ala Val Tyr Gly Thr Asp Gly Cys
                245                 250                 255

Pro Val Ser Val Glu Lys Ile Val Asn Ile Phe Asn Gly Thr Ser Cys
            260                 265                 270

Pro Ser Leu Gly Gly Lys Pro Lys Leu Phe Phe Ile Gln Ala Cys Gly
        275                 280                 285

Gly Glu Gln Lys Asp His Gly Phe Glu Val Ala Ser Thr Ser Pro Glu
    290                 295                 300

Asp Glu Ser Pro Gly Ser Asn Pro Glu Pro Asp Ala Thr Pro Phe Gln
305                 310                 315                 320

Glu Gly Leu Arg Thr Phe Asp Gln Leu Asp Ala Ile Ser Ser Leu Pro
                325                 330                 335

Thr Pro Ser Asp Ile Phe Val Ser Tyr Ser Thr Phe Pro Gly Phe Val
            340                 345                 350

Ser Trp Arg Asp Pro Lys Ser Gly Ser Trp Tyr Val Glu Thr Leu Asp
        355                 360                 365

Asp Ile Phe Glu Gln Trp Ala His Ser Glu Asp Leu Gln Ser Leu Leu
    370                 375                 380

Leu Arg Val Ala Asn Ala Val Ser Val Lys Gly Ile Tyr Lys Gln Met
385                 390                 395                 400

```
Pro Gly Cys Phe Asn Phe Leu Arg Lys Lys Leu Phe Lys Thr Ser
            405                 410                 415

<210> SEQ ID NO 2
<211> LENGTH: 282
<212> TYPE: PRT
<213> ORGANISM: Homo sapiens

<400> SEQUENCE: 2

Gly Phe Gly Asp Val Gly Ala Leu Glu Ser Leu Arg Gly Asn Ala Asp
1               5                   10                  15

Leu Ala Tyr Ile Leu Ser Met Glu Pro Cys Gly His Cys Leu Ile Ile
            20                  25                  30

Asn Asn Val Asn Phe Cys Arg Glu Ser Gly Leu Arg Thr Arg Thr Gly
        35                  40                  45

Ser Asn Ile Asp Cys Glu Lys Leu Arg Arg Arg Phe Ser Ser Leu His
    50                  55                  60

Phe Met Val Glu Val Lys Gly Asp Leu Thr Ala Lys Lys Met Val Leu
65                  70                  75                  80

Ala Leu Leu Glu Leu Ala Gln Gln Asp His Gly Ala Leu Asp Cys Cys
                85                  90                  95

Val Val Val Ile Leu Ser His Gly Cys Gln Ala Ser His Leu Gln Phe
            100                 105                 110

Pro Gly Ala Val Tyr Gly Thr Asp Gly Cys Pro Val Ser Val Glu Lys
        115                 120                 125

Ile Val Asn Ile Phe Asn Gly Thr Ser Cys Pro Ser Leu Gly Gly Lys
    130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Ser Pro Gly Ser
                165                 170                 175

Asn Pro Glu Pro Asp Ala Thr Pro Phe Gln Glu Gly Leu Arg Thr Phe
        180                 185                 190

Asp Gln Leu Asp Ala Ile Ser Ser Leu Pro Thr Pro Ser Asp Ile Phe
    195                 200                 205

Val Ser Tyr Ser Thr Phe Pro Gly Phe Val Ser Trp Arg Asp Pro Lys
    210                 215                 220

Ser Gly Ser Trp Tyr Val Glu Thr Leu Asp Asp Ile Phe Glu Gln Trp
225                 230                 235                 240

Ala His Ser Glu Asp Leu Gln Ser Leu Leu Leu Arg Val Ala Asn Ala
                245                 250                 255

Val Ser Val Lys Gly Ile Tyr Lys Gln Met Pro Gly Cys Phe Asn Phe
            260                 265                 270

Leu Arg Lys Lys Leu Phe Phe Lys Thr Ser
        275                 280

<210> SEQ ID NO 3
<211> LENGTH: 282
<212> TYPE: PRT
<213> ORGANISM: Artificial Sequence
<220> FEATURE:
<223> OTHER INFORMATION: Synthetic polypeptide sequence

<400> SEQUENCE: 3

Gly Phe Gly Asp Val Gly Ala Leu Glu Ser Leu Arg Gly Asn Ala Asp
1               5                   10                  15
```

```
Leu Ala Tyr Ile Leu Ser Met Glu Pro Cys Gly His Cys Leu Ile Ile
                20                  25                  30

Asn Asn Val Asn Phe Cys Arg Glu Ser Gly Leu Arg Thr Arg Thr Gly
            35                  40                  45

Ser Asn Ile Asp Cys Glu Lys Leu Arg Arg Arg Phe Ser Ser Leu His
 50                  55                  60

Phe Met Val Glu Val Lys Gly Asp Leu Thr Ala Lys Lys Met Val Leu
 65                  70                  75                  80

Ala Leu Leu Glu Leu Ala Gln Gln Asp His Gly Ala Leu Asp Cys Cys
                85                  90                  95

Val Val Val Ile Leu Ser His Gly Cys Gln Ala Ser His Leu Gln Phe
                100                 105                 110

Pro Gly Ala Val Tyr Gly Thr Asp Gly Cys Pro Val Ser Val Glu Lys
            115                 120                 125

Ile Val Asn Ile Phe Asn Gly Thr Ser Cys Pro Ser Leu Gly Gly Lys
130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Glu Ser Pro Gly Ser
                165                 170                 175

Asn Pro Glu Pro Asp Ala Thr Pro Phe Gln Glu Gly Leu Arg Thr Phe
            180                 185                 190

Asp Gln Leu Met Ala Ile Ser Ser Leu Pro Thr Pro Ser Asp Ile Phe
            195                 200                 205

Val Ser Tyr Ser Thr Phe Pro Gly Phe Val Ser Trp Arg Asp Pro Lys
210                 215                 220

Ser Gly Ser Trp Tyr Val Glu Thr Leu Asp Asp Ile Phe Glu Gln Trp
225                 230                 235                 240

Ala His Ser Glu Glu Leu Gln Ser Leu Leu Leu Arg Val Ala Asn Ala
                245                 250                 255

Val Ser Val Lys Gly Ile Tyr Lys Gln Met Pro Gly Cys Phe Asn Phe
            260                 265                 270

Leu Arg Lys Lys Leu Phe Phe Lys Thr Ser
            275                 280

<210> SEQ ID NO 4
<211> LENGTH: 108
<212> TYPE: PRT
<213> ORGANISM: Artificial Sequence
<220> FEATURE:
<223> OTHER INFORMATION: Synthetic polypeptide sequence

<400> SEQUENCE: 4

Gly Val Gln Val Glu Thr Ile Ser Pro Gly Asp Gly Arg Thr Phe Pro
 1               5                   10                  15

Lys Arg Gly Gln Thr Cys Val Val His Tyr Thr Gly Met Leu Glu Asp
                20                  25                  30

Gly Lys Lys Val Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
 50                  55                  60

Gln Met Ser Val Gly Gln Arg Ala Lys Leu Thr Ile Ser Pro Asp Tyr
 65                  70                  75                  80

Ala Tyr Gly Ala Thr Gly His Pro Gly Ile Ile Pro Pro His Ala Thr
                85                  90                  95
```

```
Leu Val Phe Asp Val Glu Leu Leu Lys Leu Glu Ser
            100                 105

<210> SEQ ID NO 5
<211> LENGTH: 7
<212> TYPE: PRT
<213> ORGANISM: Artificial Sequence
<220> FEATURE:
<223> OTHER INFORMATION: Synthetic polypeptide sequence

<400> SEQUENCE: 5

Gly Gly Gly Ser Gly Val Asp
1               5

<210> SEQ ID NO 6
<211> LENGTH: 397
<212> TYPE: PRT
<213> ORGANISM: Artificial Sequence
<220> FEATURE:
<223> OTHER INFORMATION: Synthetic polypeptide sequence

<400> SEQUENCE: 6

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu Ser Gly Gly Gly Ser
            100                 105                 110

Gly Val Asp Gly Phe Gly Asp Val Gly Ala Leu Glu Ser Leu Arg Gly
        115                 120                 125

Asn Ala Asp Leu Ala Tyr Ile Leu Ser Met Glu Pro Cys Gly His Cys
    130                 135                 140

Leu Ile Ile Asn Asn Val Asn Phe Cys Arg Glu Ser Gly Leu Arg Thr
145                 150                 155                 160

Arg Thr Gly Ser Asn Ile Asp Cys Glu Lys Leu Arg Arg Arg Phe Ser
                165                 170                 175

Ser Leu His Phe Met Val Glu Val Lys Gly Asp Leu Thr Ala Lys Lys
            180                 185                 190

Met Val Leu Ala Leu Leu Glu Leu Ala Gln Gln Asp His Gly Ala Leu
        195                 200                 205

Asp Cys Cys Val Val Val Ile Leu Ser His Gly Cys Gln Ala Ser His
    210                 215                 220

Leu Gln Phe Pro Gly Ala Val Tyr Gly Thr Asp Gly Cys Pro Val Ser
225                 230                 235                 240

Val Glu Lys Ile Val Asn Ile Phe Asn Gly Thr Ser Cys Pro Ser Leu
                245                 250                 255

Gly Gly Lys Pro Lys Leu Phe Phe Ile Gln Ala Cys Gly Gly Glu Gln
            260                 265                 270

Lys Asp His Gly Phe Glu Val Ala Ser Thr Ser Pro Glu Asp Glu Ser
        275                 280                 285
```

```
Pro Gly Ser Asn Pro Glu Pro Asp Ala Thr Pro Phe Gln Glu Gly Leu
    290                 295                 300

Arg Thr Phe Asp Gln Leu Met Ala Ile Ser Ser Leu Pro Thr Pro Ser
305                 310                 315                 320

Asp Ile Phe Val Ser Tyr Ser Thr Phe Pro Gly Phe Val Ser Trp Arg
                325                 330                 335

Asp Pro Lys Ser Gly Ser Trp Tyr Val Glu Thr Leu Asp Asp Ile Phe
                340                 345                 350

Glu Gln Trp Ala His Ser Glu Glu Leu Gln Ser Leu Leu Leu Arg Val
                355                 360                 365

Ala Asn Ala Val Ser Val Lys Gly Ile Tyr Lys Gln Met Pro Gly Cys
            370                 375                 380

Phe Asn Phe Leu Arg Lys Lys Leu Phe Phe Lys Thr Ser
385                 390                 395

<210> SEQ ID NO 7
<211> LENGTH: 846
<212> TYPE: DNA
<213> ORGANISM: Artificial Sequence
<220> FEATURE:
<223> OTHER INFORMATION: Synthetic polynucleotide sequence

<400> SEQUENCE: 7
ggatttggcg atgtgggcgc cctggagtct ctgagaggca atgccgatct ggcctacatc      60
ctgagcatgg agccttgcgg ccactgtctg atcatcaaca atgtgaactt ctgcagggag     120
tccggcctga gaaccaggac aggctctaat atcgactgtg agaagctgcg agaaggttc      180 tctagcctgc actttatggt ggaggtgaag ggcgatctga ccgccaagaa gatggtgctg     240
gccctgctgg agctggccca gcaggaccac ggcgccctgg attgctgcgt ggtggtcatc     300
ctgtctcacg gatgccaggc cagccacctg cagttcccag agccgtgta tggaaccgac      360 ggatgtcccg tgagcgtgga gaagatcgtg aacatcttta atggcacaag ctgcccatcc     420
ctgggaggca agccaaagct gttctttatc caggcctgtg gcggcgagca gaaggatcac     480
ggctttgagg tggccagcac ctccccagag gacgagtctc ctggcagcaa cccagagccc     540
gatgccaccc cttccaggag ggcctgcgc acatttgacc agctgatggc catctcctct      600
ctgcctaccc catccgacat cttcgtgtct tacagcacat ccctggcttc gtgagctgg      660 cgggacccca gtccggctc ttggtacgtg agacactgg acgatatctt tgagcagtgg      720
gcacacagcg aggagctgca gtccctgctg ctgagagtgg ccaacgccgt gtccgtgaag     780
ggcatctaca gcagatgcc aggctgcttc aattttctga ggaaaaaact gttcttcaaa     840
actagc                                                               846

<210> SEQ ID NO 8
<211> LENGTH: 1191
<212> TYPE: DNA
<213> ORGANISM: Artificial Sequence
<220> FEATURE:
<223> OTHER INFORMATION: Synthetic polynucleotide sequence

<400> SEQUENCE: 8
ggagtgcagg tcgaaacaat ctcacccggc gatggacgga cattccccaa aagaggacag      60
acttgcgtcg tgcattatac cggcatgctg gaggacggca agaaggtgga cagctcccgc     120
gatcggaaca agcccttcaa gtttatgctg ggcaagcagg aagtgatcag ggatgggag      180 gagggagtgg cacagatgag cgtgggacag agggcaaagc tgaccatctc cccagactac     240
```

```
gcatatggag caacaggaca ccctggaatc atcccacctc acgccacact ggtgttcgat    300
gtggagctgc tgaagctgga gtccggagga ggatctggag tggacggatt tggcgatgtg    360
ggcgccctgg agtctctgag aggcaatgcc gatctggcct acatcctgag catggagcct    420
tgcggccact gtctgatcat caacaatgtg aacttctgca gggagtccgg cctgagaacc    480
aggacaggct ctaatatcga ctgtgagaag ctgcggagaa ggttctctag cctgcacttt    540
atggtggagt gaagggcga tctgaccgcc aagaagatgg tgctggccct gctggagctg    600
gcccagcagg accacggcgc cctggattgc tgcgtggtgg tcatcctgtc tcacggatgc    660
caggccagcc acctgcagtt cccaggagcc gtgtatggaa ccgacggatg tcccgtgagc    720
gtggagaaga tcgtgaacat ctttaatggc acaagctgcc catccctggg aggcaagcca    780
aagctgttct ttatccaggc ctgtggcggc gagcagaagg atcacggctt tgaggtggcc    840
agcacctccc cagaggacga gtctcctggc agcaacccag agcccgatgc cacccctttc    900
caggagggcc tgcgcacatt tgaccagctg atggccatct cctctctgcc taccccatcc    960
gacatcttcg tgtcttacag cacattccct ggcttcgtga gctggcggga ccccaagtcc    1020
ggctcttggt acgtggagac actggacgat atctttgagc agtgggcaca cagcgaggag    1080
ctgcagtccc tgctgctgag agtggccaac gccgtgtccg tgaagggcat ctacaagcag    1140
atgccaggct gcttcaattt tctgaggaaa aaactgttct tcaaaactag c             1191
```

```
<210> SEQ ID NO 9
<211> LENGTH: 324
<212> TYPE: DNA
<213> ORGANISM: Artificial Sequence
<220> FEATURE:
<223> OTHER INFORMATION: Synthetic polynucleotide sequence

<400> SEQUENCE: 9
```

```
ggagtgcagg tcgaaacaat ctcacccggc gatggacgga cattcccaa aagaggacag       60 acttgcgtcg tgcattatac cggcatgctg gaggacggca agaaggtgga cagctcccgc    120
gatcggaaca agcccttcaa gtttatgctg ggcaagcagg aagtgatcag ggatgggag     180 gagggagtgg cacagatgag cgtgggacag agggcaaagc tgaccatctc cccagactac    240
gcatatggag caacaggaca ccctggaatc atcccacctc acgccacact ggtgttcgat    300
gtggagctgc tgaagctgga gtcc                                          324
```

```
<210> SEQ ID NO 10
<211> LENGTH: 21
<212> TYPE: DNA
<213> ORGANISM: Artificial Sequence
<220> FEATURE:
<223> OTHER INFORMATION: Synthetic polynucleotide sequence

<400> SEQUENCE: 10
```

```
ggaggaggat ctggagtgga c                                              21
```

```
<210> SEQ ID NO 11
<211> LENGTH: 846
<212> TYPE: DNA
<213> ORGANISM: Artificial Sequence
<220> FEATURE:
<223> OTHER INFORMATION: Synthetic polynucleotide sequence

<400> SEQUENCE: 11
```

```
ggatttggcg atgtgggcgc cctggagtct ctgagaggca atgccgatct ggcctacatc      60
```

```
ctgagcatgg agccttgcgg ccactgtctg atcatcaaca atgtgaactt ctgcagggag    120
tccggcctga gaaccaggac aggctctaat atcgactgtg agaagctgcg gagaaggttc    180
tctagcctgc actttatggt ggaggtgaag ggcgatctga ccgccaagaa gatggtgctg    240
gccctgctgg agctggccca gcaggaccac ggcgccctgg attgctgcgt ggtggtcatc    300
ctgtctcacg gatgccaggc cagccacctg cagttcccag gagccgtgta tggaaccgac    360
ggatgtcccg tgagcgtgga gaagatcgtg aacatcttta tggcacaag ctgcccatcc    420 ctgggaggca agccaaagct gttctttatc caggcctgtg gcggcgagca aaggatcac    480 ggctttgagg tggccagcac ctccccagag gacgagtctc ctggcagcaa cccagagccc    540
gatgccaccc ctttccagga gggcctgcgc acatttgacc agctgatggc catctcctct    600
ctgcctaccc catccgacat cttcgtgtct tacagcacat ccctggcttc cgtgagctgg    660
cgggacccca gtccggctc ttggtacgtg agacactgg acgatatctt tgagcagtgg    720
gcacacagcg aggagctgca gtccctgctg ctgagagtgg ccaacgccgt gtccgtgaag    780
ggcatctaca agcagatgcc aggctgcttc aattttctga ggaaaaaact gttcttcaaa    840
actagc                                                              846
```

<210> SEQ ID NO 12
<211> LENGTH: 25
<212> TYPE: PRT
<213> ORGANISM: Artificial Sequence
<220> FEATURE:
<223> OTHER INFORMATION: linker peptide
<220> FEATURE:
<221> NAME/KEY: MISC_FEATURE
<222> LOCATION: (6)..(10)
<223> OTHER INFORMATION: May be present or absent
<220> FEATURE:
<221> NAME/KEY: MISC_FEATURE
<222> LOCATION: (11)..(15)
<223> OTHER INFORMATION: May be present or absent
<220> FEATURE:
<221> NAME/KEY: MISC_FEATURE
<222> LOCATION: (16)..(20)
<223> OTHER INFORMATION: May be present or absent
<220> FEATURE:
<221> NAME/KEY: MISC_FEATURE
<222> LOCATION: (21)..(25)
<223> OTHER INFORMATION: May be present or absent

<400> SEQUENCE: 12

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 13
<211> LENGTH: 20
<212> TYPE: PRT
<213> ORGANISM: Artificial Sequence
<220> FEATURE:
<223> OTHER INFORMATION: linker peptide
<220> FEATURE:
<221> NAME/KEY: MISC_FEATURE
<222> LOCATION: (5)..(8)
<223> OTHER INFORMATION: May be present or absent
<220> FEATURE:
<221> NAME/KEY: MISC_FEATURE
<222> LOCATION: (9)..(12)
<223> OTHER INFORMATION: May be present or absent
<220> FEATURE:
<221> NAME/KEY: MISC_FEATURE
<222> LOCATION: (13)..(16)
<223> OTHER INFORMATION: May be present or absent

```
<220> FEATURE:
<221> NAME/KEY: MISC_FEATURE
<222> LOCATION: (17)..(20)
<223> OTHER INFORMATION: May be present or absent

<400> SEQUENCE: 13

Gly Gly Gly Ser Gly Gly Gly Ser Gly Gly Gly Ser Gly Gly Gly Ser
1               5                   10                  15

Gly Gly Gly Ser
            20

<210> SEQ ID NO 14
<211> LENGTH: 18
<212> TYPE: PRT
<213> ORGANISM: Artificial Sequence
<220> FEATURE:
<223> OTHER INFORMATION: linker peptide

<400> SEQUENCE: 14

Gly Ser Thr Ser Gly Ser Gly Lys Pro Gly Ser Gly Glu Gly Ser Thr
1               5                   10                  15

Lys Gly

<210> SEQ ID NO 15
<211> LENGTH: 15
<212> TYPE: PRT
<213> ORGANISM: Artificial Sequence
<220> FEATURE:
<223> OTHER INFORMATION: linker peptide

<400> SEQUENCE: 15

Gly Gly Gly Gly Ser Gly Gly Gly Ser Gly Gly Gly Gly Ser
1               5                   10                  15

<210> SEQ ID NO 16
<211> LENGTH: 23
<212> TYPE: PRT
<213> ORGANISM: Artificial Sequence
<220> FEATURE:
<223> OTHER INFORMATION: linker peptide
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (21)..(23)
<223> OTHER INFORMATION: Xaa can be any naturally occurring amino acid

<400> SEQUENCE: 16

Xaa Xaa Xaa Gly Lys Pro Gly Ser Gly Glu Xaa Xaa Xaa Gly Lys Pro
1               5                   10                  15

Gly Ser Gly Glu Xaa Xaa Xaa
            20

<210> SEQ ID NO 17
<211> LENGTH: 6
<212> TYPE: PRT
<213> ORGANISM: Artificial Sequence
<220> FEATURE:
<223> OTHER INFORMATION: linker peptide

<400> SEQUENCE: 17
```

```
Lys Pro Gly Ser Gly Glu
1               5

<210> SEQ ID NO 18
<211> LENGTH: 7
<212> TYPE: PRT
<213> ORGANISM: Artificial Sequence
<220> FEATURE:
<223> OTHER INFORMATION: linker peptide

<400> SEQUENCE: 18

Gly Lys Pro Gly Ser Gly Glu
1               5

<210> SEQ ID NO 19
<211> LENGTH: 7
<212> TYPE: PRT
<213> ORGANISM: Artificial Sequence
<220> FEATURE:
<223> OTHER INFORMATION: linker peptide

<400> SEQUENCE: 19

Gly Lys Pro Gly Ser Gly Gly
1               5

<210> SEQ ID NO 20
<211> LENGTH: 15
<212> TYPE: PRT
<213> ORGANISM: Artificial Sequence
<220> FEATURE:
<223> OTHER INFORMATION: linker peptide

<400> SEQUENCE: 20

Gly Gly Gly Ser Gly Lys Pro Gly Ser Gly Glu Gly Gly Gly Ser
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: linker peptide

<400> SEQUENCE: 21

Gly Gly Gly Ser Gly Lys Pro Gly Ser Gly Glu Gly Gly Gly Gly Ser
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: linker peptide

<400> SEQUENCE: 22

Gly Gly Gly Gly Ser Gly Lys Pro Gly Ser Gly Gly Gly Gly Ser
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: linker peptide

<400> SEQUENCE: 23

Gly Gly Gly Gly Ser Gly Lys Pro Gly Ser Gly Glu Gly Gly Ser
```

<210> SEQ ID NO 24
<211> LENGTH: 16
<212> TYPE: PRT
<213> ORGANISM: Artificial Sequence
<220> FEATURE:
<223> OTHER INFORMATION: linker peptide

<400> SEQUENCE: 24

Gly Gly Gly Gly Ser Gly Lys Pro Gly Ser Gly Glu Gly Gly Gly Ser
1               5                   10                  15

<210> SEQ ID NO 25
<211> LENGTH: 17
<212> TYPE: PRT
<213> ORGANISM: Artificial Sequence
<220> FEATURE:
<223> OTHER INFORMATION: linker peptide

<400> SEQUENCE: 25

Gly Gly Gly Gly Ser Gly Lys Pro Gly Ser Gly Glu Gly Gly Gly Gly
1               5                   10                  15

Ser

<210> SEQ ID NO 26
<211> LENGTH: 10
<212> TYPE: PRT
<213> ORGANISM: Artificial Sequence
<220> FEATURE:
<223> OTHER INFORMATION: linker peptide

<400> SEQUENCE: 26

Gly Ser Gly Lys Pro Gly Ser Gly Glu Gly
1               5                   10

<210> SEQ ID NO 27
<211> LENGTH: 8
<212> TYPE: PRT
<213> ORGANISM: Artificial Sequence
<220> FEATURE:
<223> OTHER INFORMATION: linker peptide

<400> SEQUENCE: 27

Gly Lys Pro Gly Ser Gly Glu Gly
1               5

<210> SEQ ID NO 28
<211> LENGTH: 8
<212> TYPE: PRT
<213> ORGANISM: Artificial Sequence
<220> FEATURE:
<223> OTHER INFORMATION: linker peptide

<400> SEQUENCE: 28

Ser Gly Lys Pro Gly Ser Gly Glu
1               5

<210> SEQ ID NO 29
<211> LENGTH: 5
<212> TYPE: PRT
<213> ORGANISM: Artificial Sequence
<220> FEATURE:
<223> OTHER INFORMATION: linker peptide

<400> SEQUENCE: 29

```
Lys Pro Gly Ser Gly
1               5

<210> SEQ ID NO 30
<211> LENGTH: 15
<212> TYPE: PRT
<213> ORGANISM: Artificial Sequence
<220> FEATURE:
<223> OTHER INFORMATION: linker peptide

<400> SEQUENCE: 30

Ser Thr Ser Gly Ser Gly Lys Pro Gly Ser Gly Glu Gly Ser Thr
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: linker peptide

<400> SEQUENCE: 31

Gly Gly Gly Gly Ser Gly Gly Gly Gly Ser Gly Gly Gly Gly Ser Gly
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: linker peptide

<400> SEQUENCE: 32

Gly Gly Gly Gly Gly Ser Gly Gly Gly Gly Ser Gly Gly Gly Gly Ser
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: linker peptide

<400> SEQUENCE: 33

Gly Gly Gly Gly Ser Gly Gly Gly Gly Ser Gly Gly Gly Gly Gly Ser
1               5                   10                  15
```